US011191627B2

(12) United States Patent
Boraas et al.

(10) Patent No.: US 11,191,627 B2
(45) Date of Patent: Dec. 7, 2021

(54) ORTHOPEDIC BRACE FOR ANIMALS

(71) Applicant: DJO, LLC, Vista, CA (US)

(72) Inventors: Chris Boraas, Alexandria, MN (US); Kristian Gamble, Minneapolis, MN (US)

(73) Assignee: DJO, LLC, Vista, CA (US)

( * ) Notice: Subject to any disclaimer, the term of this patent is extended or adjusted under 35 U.S.C. 154(b) by 1285 days.

(21) Appl. No.: 15/219,792

(22) Filed: Jul. 26, 2016

(65) Prior Publication Data

US 2017/0014216 A1    Jan. 19, 2017

Related U.S. Application Data

(63) Continuation of application No. 13/839,737, filed on Mar. 15, 2013, now Pat. No. 9,408,738.

(60) Provisional application No. 61/678,426, filed on Aug. 1, 2012.

(51) Int. Cl.
*A61F 5/00* (2006.01)
*A61D 9/00* (2006.01)
*A61F 5/01* (2006.01)

(52) U.S. Cl.
CPC .................. *A61D 9/00* (2013.01); *A61F 5/01* (2013.01); *A61F 5/0102* (2013.01)

(58) Field of Classification Search
CPC ........ A61F 5/01; A61F 5/0102; A61F 5/0104; A61F 5/0106; A61F 5/0109; A61F 5/0111; A61F 5/0113; A61F 5/0116; A61F 5/0118; A61F 5/0123; A61F 5/0125; A61F 5/0127; A61F 5/013; A61F 5/058; A61F 5/05825; A61F 5/05841; A61F 5/0585; A61F 5/05858; A61F 2005/0132; A61F 2005/0134; A61F 2005/0137; A61F 2005/0139; A61F 2005/0141; A61F 2005/0144; A61F 2005/0146; A61F 2005/0148; A61F 2005/0151; A61F 2005/0153; A61F 2005/0155; A61F 2005/0158; A61F 2005/0165; A61F 2005/0167; A61F 2005/0172; A61F 7/08;
(Continued)

(56) References Cited

U.S. PATENT DOCUMENTS

| 57,283 A | 8/1866 | Brown |
|---|---|---|
| D19,360 S | 10/1889 | Sanders |
| 482,647 A | 9/1892 | Obear |

(Continued)

FOREIGN PATENT DOCUMENTS

| EP | 0 619 102 | 10/1994 |
|---|---|---|
| JP | 2004-065912 | 3/2004 |

*Primary Examiner* — Kim M Lewis
(74) *Attorney, Agent, or Firm* — Knobbe, Martens, Olson & Bear LLP

(57) ABSTRACT

Orthopedic braces and splints for use on a limb of an animal, that provide stability for unstable joints and limbs for short or long term support and function. These orthoses are designed to prevent the occurrence of or reduce the severity of, a joint injury. These braces and splints can also be fitted immediately after corrective surgery, and can support and stabilize the joint while assisting or restricting the range of motion. Various embodiments of the orthoses are modular, thermoformable and may include an adjustable tensioning system, which in combination provide a custom fit for a wide variety of animals and injuries.

20 Claims, 17 Drawing Sheets

(58) Field of Classification Search
CPC .... A61D 9/00; A61D 2003/006; A01K 13/00; A01K 13/006; A01K 13/007
See application file for complete search history.

(56) References Cited

U.S. PATENT DOCUMENTS

| | | |
|---|---|---|
| D35,545 S | 12/1901 | Schaefer |
| 911,243 A * | 2/1909 | Johannesen .......... A61F 5/0123 602/16 |
| 975,734 A | 11/1910 | Tebeau |
| 1,082,542 A | 12/1913 | Manson |
| 1,360,840 A | 11/1920 | White |
| 1,477,070 A | 3/1922 | Martin |
| 1,471,948 A | 10/1923 | Cox et al. |
| 1,583,606 A | 5/1926 | Roussel |
| 2,070,810 A | 2/1937 | Saling |
| 2,181,689 A | 11/1939 | Bell |
| 2,206,404 A | 7/1940 | Jones |
| 2,477,040 A | 3/1945 | Brown et al. |
| 2,554,337 A | 5/1951 | Lampert |
| 2,736,314 A | 2/1956 | Hale |
| 2,759,475 A | 8/1956 | Swaay |
| 2,818,063 A | 12/1957 | Smith et al. |
| 2,904,040 A | 9/1959 | Hale |
| D198,069 S | 4/1964 | Connelly |
| D203,018 S | 11/1965 | Helferich |
| 3,230,952 A | 1/1966 | Reyes Terron |
| 3,302,642 A | 2/1967 | Allen |
| 3,306,284 A | 2/1967 | McKinley |
| 3,313,297 A | 4/1967 | Applegate et al. |
| 3,320,950 A | 5/1967 | McElvenny |
| 3,420,231 A | 1/1969 | Edenbaum |
| 3,490,444 A | 1/1970 | Larson |
| 3,512,523 A | 5/1970 | Barnett |
| 3,692,023 A | 9/1972 | Phillips et al. |
| 3,788,307 A | 1/1974 | Kistner |
| 3,896,843 A | 7/1975 | Millar et al. |
| 3,906,943 A | 9/1975 | Arluck |
| 3,916,885 A | 11/1975 | Gaylord, Jr. |
| 3,924,272 A | 12/1975 | Allen et al. |
| 4,006,741 A | 2/1977 | Arluck |
| 4,019,505 A | 4/1977 | Wartman |
| 4,136,686 A | 1/1979 | Arluck |
| 4,169,469 A | 10/1979 | Arluck |
| 4,193,395 A | 3/1980 | Gruber |
| D256,055 S | 7/1980 | Finnieston |
| 4,235,228 A | 11/1980 | Gaylord et al. |
| 4,240,415 A | 12/1980 | Wartman |
| D259,955 S | 7/1981 | Helferich |
| 4,286,586 A | 9/1981 | Potts |
| 4,316,457 A | 2/1982 | Liegeois |
| D266,288 S | 9/1982 | Coon |
| 4,379,463 A | 4/1983 | Meier et al. |
| D270,284 S | 8/1983 | Lindh et al. |
| 4,427,002 A | 1/1984 | Baron et al. |
| 4,441,711 A | 4/1984 | Dubar et al. |
| 4,442,834 A | 4/1984 | Tucker et al. |
| 4,454,873 A | 6/1984 | Lautenberg et al. |
| 4,471,993 A | 9/1984 | Watson |
| 4,473,671 A | 9/1984 | Green |
| 4,482,414 A | 11/1984 | Schonberger |
| 4,483,333 A | 11/1984 | Wartman |
| 4,510,927 A | 4/1985 | Peters |
| 4,531,241 A | 7/1985 | Berger |
| 4,572,167 A | 2/1986 | Brunswick |
| 4,584,993 A | 4/1986 | Nelson |
| 4,600,618 A | 7/1986 | Raychok, Jr. et al. |
| D287,640 S | 1/1987 | Primiano |
| 4,661,535 A | 4/1987 | Borroff |
| 4,726,361 A * | 2/1988 | Farley ...................... A61D 9/00 602/23 |
| 4,765,319 A | 8/1988 | Finnieston et al. |
| 4,770,299 A | 9/1988 | Parker |
| 4,784,123 A | 11/1988 | Robeson |
| 4,827,915 A | 5/1989 | Gorsen |
| 4,872,448 A | 10/1989 | Johnson |
| 4,888,225 A | 12/1989 | Sandvig et al. |
| 4,912,174 A | 3/1990 | Grouiller |
| 4,946,726 A | 8/1990 | Sandvig et al. |
| 4,955,368 A | 9/1990 | Heimann |
| 5,031,607 A | 7/1991 | Peters |
| 5,038,759 A | 8/1991 | Morgenstern |
| 5,058,576 A | 10/1991 | Grim et al. |
| 5,098,778 A | 3/1992 | Minnick |
| D326,719 S | 6/1992 | Eghamn |
| 5,151,315 A | 9/1992 | Ponnet |
| 5,158,098 A | 10/1992 | Jalalian |
| 5,180,361 A | 1/1993 | Moore et al. |
| 5,230,698 A | 7/1993 | Garth |
| 5,316,604 A | 5/1994 | Fell |
| RE34,714 E | 8/1994 | Burns et al. |
| 5,364,693 A | 11/1994 | Moren et al. |
| 5,366,439 A | 11/1994 | Peters |
| D357,745 S | 4/1995 | Radwell |
| 5,409,761 A | 4/1995 | Langley |
| 5,415,622 A | 5/1995 | Kelley |
| D363,780 S | 10/1995 | Darby et al. |
| 5,454,780 A | 10/1995 | Duback et al. |
| 5,520,529 A | 5/1996 | Heckel |
| D373,639 S | 9/1996 | McKie |
| 5,554,104 A | 9/1996 | Grim |
| 5,599,288 A | 2/1997 | Shirley et al. |
| 5,624,386 A | 4/1997 | Tailor et al. |
| 5,632,722 A | 5/1997 | Tweardy et al. |
| 5,688,229 A | 11/1997 | Bauer |
| 5,737,774 A | 4/1998 | Petty-Saphon et al. |
| 5,752,873 A | 5/1998 | Morris |
| 5,752,926 A | 5/1998 | Larson et al. |
| D395,514 S | 6/1998 | Stano |
| 5,763,047 A | 6/1998 | Green |
| 5,769,804 A | 6/1998 | Harris et al. |
| 5,807,291 A | 9/1998 | Larson et al. |
| 5,819,312 A | 10/1998 | Snyder et al. |
| 5,823,984 A | 10/1998 | Silverberg |
| 5,826,304 A | 10/1998 | Carlson |
| 5,830,167 A | 11/1998 | Jung |
| D405,180 S | 2/1999 | Reina |
| 5,865,778 A | 2/1999 | Johnson |
| 5,882,322 A | 3/1999 | Kim et al. |
| 5,902,259 A | 5/1999 | Wilkerson |
| 5,926,843 A | 7/1999 | Winchester |
| 5,934,599 A | 8/1999 | Hammerslag |
| 5,951,504 A | 9/1999 | Iglesias et al. |
| 5,971,946 A | 10/1999 | Quinn et al. |
| 5,982,285 A | 11/1999 | Bueche et al. |
| 6,042,557 A | 3/2000 | Ferguson et al. |
| 6,053,884 A | 4/2000 | Peters |
| 6,056,671 A | 5/2000 | Marmer |
| 6,056,713 A | 5/2000 | Hayashi |
| RE36,745 E | 6/2000 | Rudy, Jr. et al. |
| 6,093,161 A | 7/2000 | Vlaeyen et al. |
| 6,110,134 A | 8/2000 | Clark, Jr. et al. |
| 6,146,240 A | 11/2000 | Morris |
| D436,177 S | 1/2001 | Miller |
| 6,168,966 B1 | 1/2001 | Grim et al. |
| 6,179,798 B1 | 1/2001 | Nelson |
| D437,416 S | 2/2001 | Slautterback |
| 6,186,966 B1 | 2/2001 | Grim et al. |
| 6,202,953 B1 | 3/2001 | Hammerslag |
| 6,254,560 B1 | 7/2001 | Tweardy et al. |
| 6,289,558 B1 | 9/2001 | Hammerslag |
| 6,322,529 B1 | 11/2001 | Chung |
| 6,325,772 B1 | 12/2001 | Scheuermann et al. |
| 6,358,220 B1 | 3/2002 | Langen et al. |
| 6,393,810 B1 * | 5/2002 | Mier .................... A01K 13/007 168/1 |
| 6,416,074 B1 | 7/2002 | Maravets et al. |
| 6,423,020 B1 | 7/2002 | Koledin |
| D463,565 S | 9/2002 | Slautterback |
| 6,470,832 B1 * | 10/2002 | Peacock ............... A01K 13/007 119/850 |
| 6,509,078 B1 | 1/2003 | Beckmann |
| 6,520,925 B1 | 2/2003 | Thibodo, Jr. |
| D473,653 S | 4/2003 | Weaver, II et al. |

(56) References Cited

U.S. PATENT DOCUMENTS

| | | |
|---|---|---|
| D477,088 S | 7/2003 | Brown et al. |
| D477,409 S | 7/2003 | Mills et al. |
| D477,410 S | 7/2003 | Wiggins et al. |
| 6,602,215 B1 | 8/2003 | Richie, Jr. |
| 6,663,581 B1 | 12/2003 | Calabrese |
| D492,787 S | 7/2004 | Weaver, II et al. |
| 6,779,282 B2 | 8/2004 | Grohninger |
| D496,465 S | 9/2004 | Weaver, II |
| D500,855 S | 1/2005 | Pick et al. |
| 6,843,190 B1 | 1/2005 | LaPierre-McAfee |
| 6,872,188 B2 | 3/2005 | Caille et al. |
| D505,727 S | 5/2005 | Krahner et al. |
| 6,893,410 B1 | 5/2005 | Hely |
| 6,922,917 B2 | 8/2005 | Kerns et al. |
| 6,960,176 B1 | 11/2005 | Hely et al. |
| 7,001,348 B2 | 2/2006 | Garth et al. |
| D518,895 S | 4/2006 | Weaver, II et al. |
| D519,211 S | 4/2006 | Doty et al. |
| 7,025,737 B2 | 4/2006 | Modglin |
| 7,041,073 B1 | 5/2006 | Patron |
| 7,056,298 B1 | 6/2006 | Weber |
| 7,082,701 B2 | 8/2006 | Dalgaard et al. |
| 7,083,585 B2 | 8/2006 | Latham |
| 7,090,653 B2 | 8/2006 | Moeller |
| D530,016 S | 10/2006 | Sroufe et al. |
| 7,141,031 B2 | 11/2006 | Garth et al. |
| 7,182,741 B2 | 2/2007 | Porrata et al. |
| 7,204,817 B1 | 4/2007 | Toronto et al. |
| D542,919 S | 5/2007 | Leatt |
| 7,217,060 B2 | 5/2007 | Ingimarsson |
| D550,370 S | 9/2007 | Peters et al. |
| D552,743 S | 10/2007 | Verkade et al. |
| D552,744 S | 10/2007 | Verkade et al. |
| D558,883 S | 1/2008 | Ortiz |
| 7,316,660 B1 | 1/2008 | Modglin |
| 7,329,229 B2 | 2/2008 | Scheinberg et al. |
| D565,189 S | 3/2008 | Gramza et al. |
| 7,392,602 B2 | 7/2008 | Reagan et al. |
| 7,399,288 B2 | 7/2008 | Chao |
| D580,064 S | 11/2008 | Lin et al. |
| D580,555 S | 11/2008 | Lin et al. |
| 7,449,006 B2 | 11/2008 | Wolanske |
| 7,470,243 B2 | 12/2008 | Garth |
| D584,822 S | 1/2009 | Weber |
| 7,507,215 B2 | 3/2009 | Ryan |
| 7,591,050 B2 | 9/2009 | Hammerslag |
| 7,597,671 B2 | 10/2009 | Baumgartner et al. |
| 7,608,052 B1 | 10/2009 | Baker |
| 7,645,250 B2 | 1/2010 | Koby et al. |
| 7,674,234 B2 | 3/2010 | Calco et al. |
| D616,556 S | 5/2010 | Hu |
| D617,464 S | 6/2010 | Weaver, II et al. |
| 7,727,172 B2 | 6/2010 | Wang |
| D626,242 S | 10/2010 | Sagnip et al. |
| D626,244 S | 10/2010 | Sagnip et al. |
| D628,300 S | 11/2010 | Caden |
| D628,696 S | 12/2010 | Robertson |
| D629,115 S | 12/2010 | Robertson |
| 7,846,118 B2 | 12/2010 | Sandhu |
| 7,854,714 B1 | 12/2010 | Weber et al. |
| 7,874,997 B2 | 1/2011 | Jaccard |
| D632,401 S | 2/2011 | Stevens |
| 7,883,485 B2 | 2/2011 | Moenning et al. |
| D633,622 S | 3/2011 | Chiang |
| D633,623 S | 3/2011 | Leatt et al. |
| D635,269 S | 3/2011 | Franke et al. |
| D635,270 S | 3/2011 | Chiang |
| D635,682 S | 4/2011 | Chiang |
| D636,494 S | 4/2011 | Garth et al. |
| D638,948 S | 5/2011 | Janzon |
| 7,942,837 B2 | 5/2011 | Clark et al. |
| 7,950,112 B2 | 5/2011 | Hammerslag et al. |
| D639,965 S | 6/2011 | Wehsely-Swiczinsky |
| 7,954,204 B2 | 6/2011 | Hammerslag et al. |
| 7,955,287 B2 | 6/2011 | Frangi |
| D641,482 S | 7/2011 | Robertson et al. |
| D641,483 S | 7/2011 | Robertson et al. |
| D643,978 S | 8/2011 | Abajo Alonso et al. |
| 7,992,261 B2 | 8/2011 | Hammerslag et al. |
| D647,623 S | 10/2011 | Thorgilsdottir et al. |
| D647,624 S | 10/2011 | Thorgilsdottir et al. |
| D649,648 S | 11/2011 | Cavalieri et al. |
| D649,649 S | 11/2011 | Leatt et al. |
| D649,650 S | 11/2011 | Wehsely-Swiczinsky |
| 8,057,417 B2 | 11/2011 | Imai |
| D650,485 S | 12/2011 | Jaccard |
| D652,937 S | 1/2012 | Robertson et al. |
| 8,091,182 B2 | 1/2012 | Hammerslag et al. |
| D654,180 S | 2/2012 | Weaver, II |
| D657,062 S | 4/2012 | Chiang |
| D657,063 S | 4/2012 | Chiang |
| D663,850 S | 7/2012 | Joseph |
| D663,851 S | 7/2012 | Joseph |
| D663,852 S | 7/2012 | Joseph |
| D664,259 S | 7/2012 | Joseph |
| D665,088 S | 8/2012 | Joseph |
| D666,301 S | 8/2012 | Joseph |
| D666,302 S | 8/2012 | Joseph |
| 8,246,560 B2 | 8/2012 | Gaylord et al. |
| 8,277,401 B2 | 10/2012 | Hammerslag et al. |
| 8,303,527 B2 | 11/2012 | Joseph |
| D687,556 S | 8/2013 | Joseph |
| D687,566 S | 8/2013 | Joseph |
| 8,856,972 B2 | 10/2014 | Kirshon |
| 8,951,217 B2 | 2/2015 | Joseph |
| 9,295,748 B2 | 3/2016 | Joseph |
| 9,408,738 B2 | 8/2016 | Boraas et al. |
| 9,561,128 B2 * | 2/2017 | Joseph .................... A61F 5/01 |
| 10,285,845 B2 | 5/2019 | Joseph |
| 10,463,544 B2 | 11/2019 | Joseph |
| 10,517,749 B2 | 12/2019 | Joseph |
| 2002/0068890 A1 | 6/2002 | Schwenn et al. |
| 2002/0095750 A1 | 7/2002 | Hammerslag |
| 2002/0148461 A1 | 10/2002 | Heinz et al. |
| 2002/0161114 A1 | 10/2002 | Gunatillake et al. |
| 2003/0178404 A1 | 9/2003 | Dimartino et al. |
| 2003/0204938 A1 | 11/2003 | Hammerslag |
| 2004/0024337 A1 | 2/2004 | Tseng et al. |
| 2004/0034316 A1 | 2/2004 | Castro |
| 2004/0255955 A1 * | 12/2004 | Daly .................... A61D 9/00 |
| | | 128/869 |
| 2005/0033207 A1 | 2/2005 | Anders |
| 2005/0034686 A1 | 2/2005 | Spatt |
| 2005/0043664 A1 | 2/2005 | Reaux |
| 2005/0101898 A1 | 5/2005 | Cohen |
| 2005/0197606 A1 | 9/2005 | Preire |
| 2005/0251074 A1 | 11/2005 | Latham |
| 2005/0273030 A1 | 12/2005 | Koby et al. |
| 2005/0281999 A1 | 12/2005 | Hofmann et al. |
| 2006/0051402 A1 | 3/2006 | Bogardus et al. |
| 2006/0052730 A1 | 3/2006 | Hargrave et al. |
| 2006/0062991 A1 | 3/2006 | Sendijarevic et al. |
| 2006/0129075 A1 | 6/2006 | Scheinberg et al. |
| 2006/0155226 A1 | 7/2006 | Grim et al. |
| 2006/0156517 A1 | 7/2006 | Hammerslag et al. |
| 2006/0173390 A1 | 8/2006 | Van Wyk et al. |
| 2007/0004993 A1 | 1/2007 | Coppens et al. |
| 2007/0077393 A1 | 4/2007 | Chiang et al. |
| 2007/0179417 A1 | 8/2007 | Schwenn et al. |
| 2008/0060167 A1 | 3/2008 | Hammerslag et al. |
| 2008/0060168 A1 | 3/2008 | Hammerslag et al. |
| 2008/0066272 A1 * | 3/2008 | Hammerslag .......... A43C 11/14 |
| | | 24/712 |
| 2008/0066345 A1 | 3/2008 | Hammerslag et al. |
| 2008/0066346 A1 | 3/2008 | Hammerslag et al. |
| 2008/0082033 A1 | 4/2008 | Ortiz |
| 2008/0083135 A1 | 4/2008 | Hammerslag et al. |
| 2008/0177210 A1 | 7/2008 | McDevitt Larson |
| 2008/0262400 A1 | 10/2008 | Clark et al. |
| 2009/0082707 A1 | 3/2009 | Rumsey |
| 2009/0192425 A1 | 7/2009 | Garth et al. |
| 2009/0192427 A1 | 7/2009 | Brown et al. |
| 2009/0204042 A1 | 8/2009 | Park |
| 2009/0204047 A1 | 8/2009 | MacArthur |

(56) References Cited

U.S. PATENT DOCUMENTS

| | | |
|---|---|---|
| 2009/0264802 A1 | 10/2009 | Chen |
| 2010/0168630 A1 | 7/2010 | Cropper et al. |
| 2010/0185130 A1 | 7/2010 | Rizo Patron |
| 2010/0262054 A1 | 10/2010 | Summit et al. |
| 2010/0268139 A1 | 10/2010 | Garth |
| 2010/0268140 A1 | 10/2010 | Berlese |
| 2010/0268141 A1 | 10/2010 | Bannister |
| 2010/0299959 A1 | 12/2010 | Hammerslag et al. |
| 2010/0318010 A1 | 12/2010 | Sandifer et al. |
| 2011/0034844 A1 | 2/2011 | Thorgilsdottir et al. |
| 2011/0082402 A1 | 4/2011 | Oddou et al. |
| 2011/0130694 A1 | 6/2011 | Livolsi et al. |
| 2011/0213284 A1 | 9/2011 | Garth et al. |
| 2011/0313389 A1 | 12/2011 | Wood et al. |
| 2012/0065562 A1 | 3/2012 | Kaphingst |
| 2013/0102940 A1 | 4/2013 | Joseph |
| 2013/0260080 A1 | 10/2013 | Roberts |
| 2013/0274744 A1* | 10/2013 | Ikemizu ............. A61B 17/6441 606/54 |
| 2013/0338554 A1* | 12/2013 | Pflaster ................ A61B 5/1121 602/16 |
| 2014/0039367 A1* | 2/2014 | Boraas .................. A61F 5/0102 602/7 |
| 2014/0135672 A1 | 5/2014 | Joseph et al. |
| 2015/0119775 A1 | 4/2015 | Gildersleeve et al. |
| 2015/0238343 A1 | 8/2015 | Joseph |
| 2018/0055671 A1 | 3/2018 | Joseph |
| 2019/0254861 A1 | 8/2019 | Joseph |
| 2020/0237547 A1 | 7/2020 | Joseph |

* cited by examiner

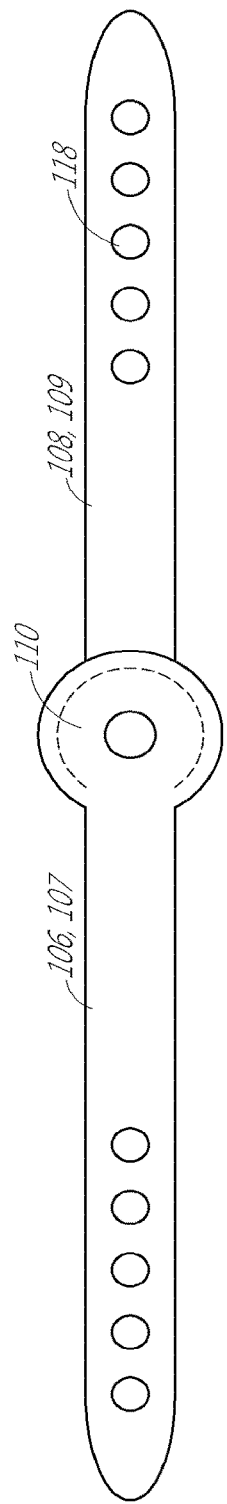
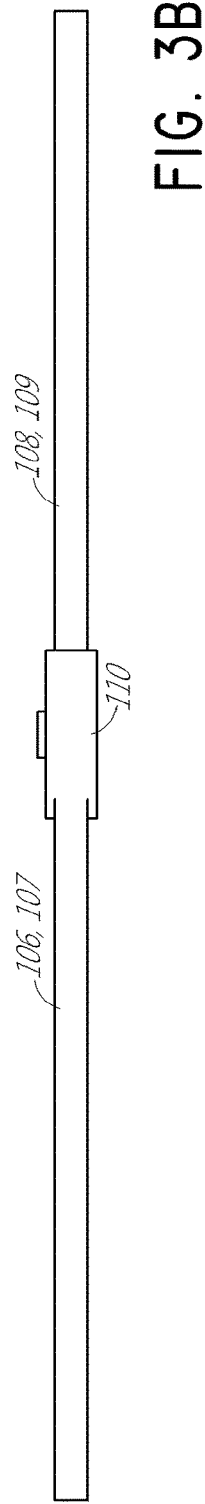
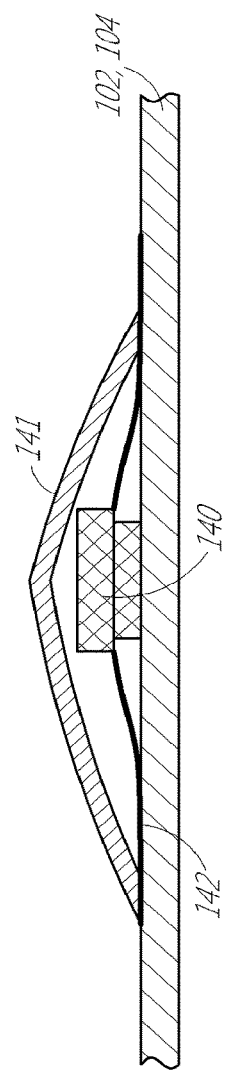

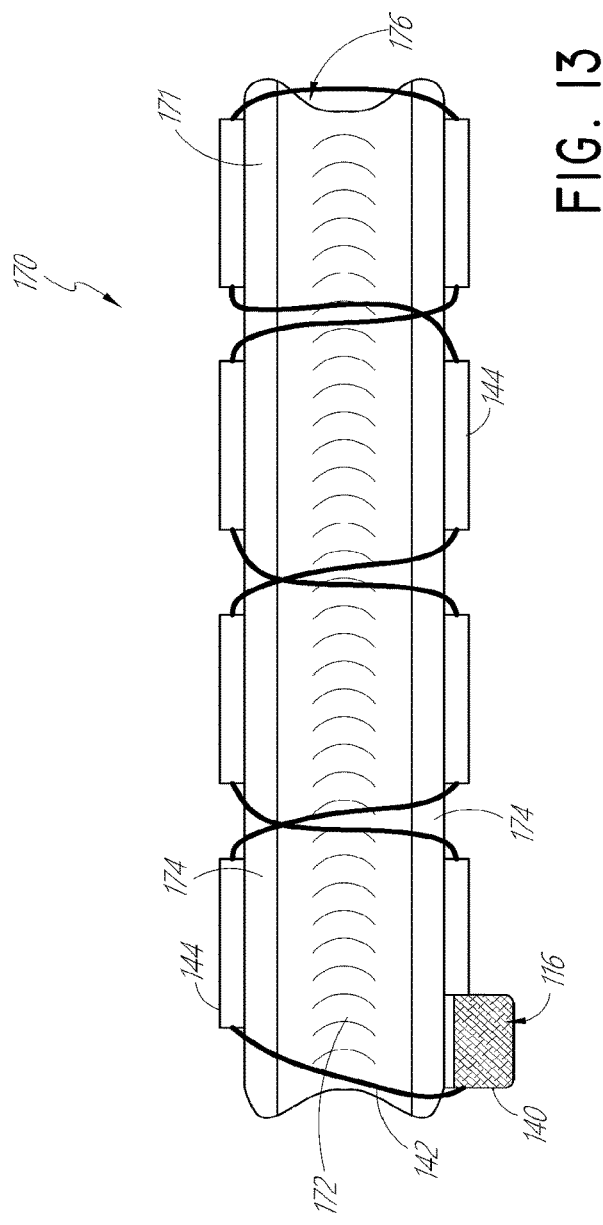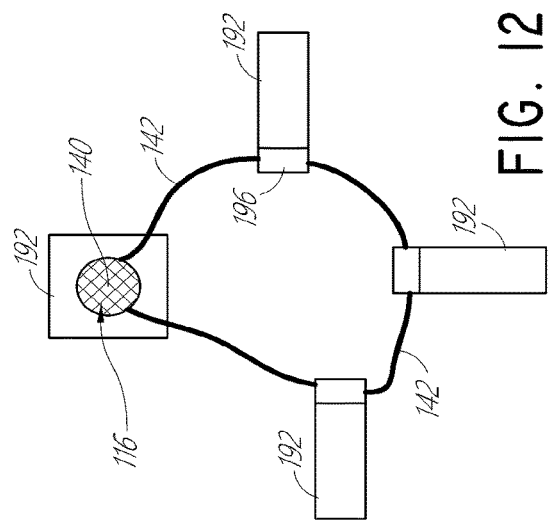

FIG. 16
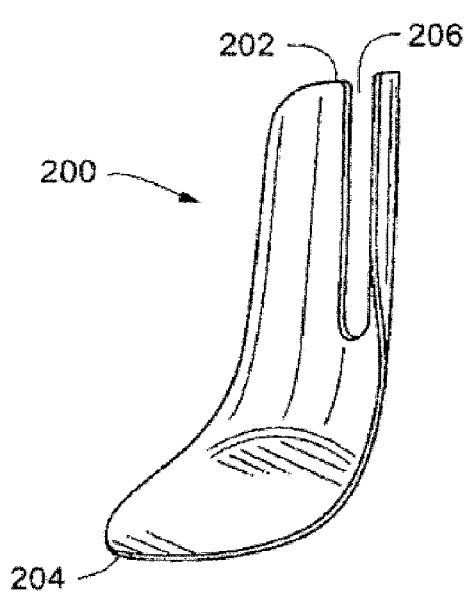
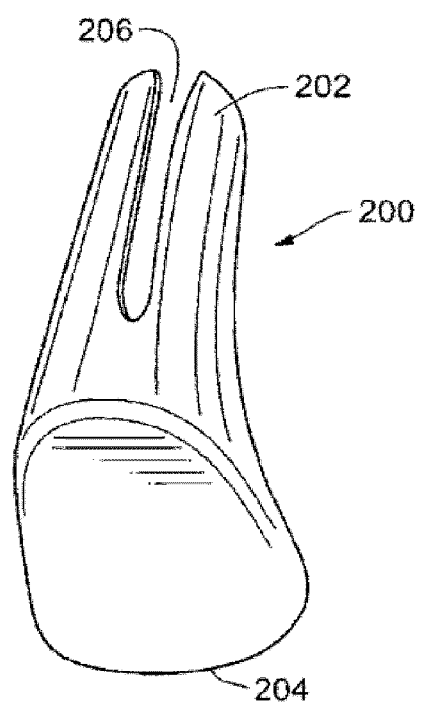
FIG. 17

ORTHOPEDIC BRACE FOR ANIMALS

INCORPORATION BY REFERENCE TO PRIORITY APPLICATIONS

This application is a continuation of U.S. application Ser. No. 13/839,737, filed Mar. 3, 2013, entitled "ORTHOPEDIC BRACE FOR ANIMALS," which claims the benefit of U.S. Provisional Application No. 61/678,426, filed Aug. 1, 2012, also entitled "ORTHOPEDIC BRACE FOR ANIMALS," each of which is incorporated by reference herein in its entirety and for all purposes. Any and all applications for which a foreign or domestic priority claim is identified in the Application Data Sheet as filed with the present application are hereby incorporated by reference under 37 CFR 1.57.

FIELD OF THE INVENTION

The present invention relates generally to a custom fit orthosis. More particularly, the present invention relates to heat formable orthoses for animals to treat a variety of injuries.

BACKGROUND OF THE INVENTION

Animals commonly suffer joint injuries of the limbs. These injuries frequently require surgery and/or use of orthoses such as braces or splints to support and stabilize the joint. Braces and splints provide immobilization of the limb, by resisting flexion and extension of the joint, and also provide stabilization by maintaining proper alignment of the joint in relation to the rest of the limb while providing support to the joint.

Braces and splints are used to provide support and stabilization to an animal's fore and/or rear limbs due to injury or surgery. A common joint injury seen in animals, often requiring the use of a brace or splint, is a torn ligament, particularly of the cranial cruciate ligament (CCL). The CCL is located in the knee or stifle joint of an animal's rear leg and, in canines, a CCL injury is the most common torn ligament injury. It is estimated that, per year, 1.2 million dogs undergo surgery to repair the CCL at a cost of approximately $1.3 billion. It is further estimated that of the 73 million dogs in the United States, 37% of large breed dogs and 45% of small breed dogs rupture their CCL.

Various types of animal orthoses are currently available and run the gamut from completely immobilizing the limb to allowing limited limb mobility. Braces and splints that immobilize the limb are generally one continuous structure and are universally sized to fit animals within a certain size range. The universal devices are generally not modified to fit an individual animal or can only be slightly modified and are generally inexpensive.

Braces that allow a fuller range of motion are more expensive and generally consist of two or more pieces that are joined to form a hinge or joined by a hinge. Hinged braces can be universally sized or are custom made and fitted. Hinged braces are generally bulky, cumbersome, and heavy. The upper portion is generally constructed of a flexible plastic or rubber material that partially surrounds the upper limb and is held in place with at least one band of VELCRO or straps. The bottom portion is normally connected to the upper portion with a hinge mechanism. The bottom portion is held to the lower limb using at least one VELCRO band or straps. In addition, the hinged braces can have stabilizing bars formed into the brace.

A common problem with the universal braces and splints, whether hinged or the one-piece construction, is that the brace or splint is not properly fitted resulting in either too much compression of the limb or too much float within the brace or splint. Another common problem is that the lineal proportions can also be out of scale in comparison to the animals limb so that the brace or splint is either too long or too short.

Custom made and fitted braces and splints normally require casting, molding, and fitting activities over a period of weeks requiring multiple trips to the veterinarian. One example of a custom fitted brace is manufactured by Ace Ortho Solutions. This jointed brace is custom fitted using a casting, molding, and fitting process which can take at least two weeks. A casting is made, by a veterinarian, of the animals limb and is mailed to an off-site laboratory. The brace is shaped from co-polymer plastic based on the casting of the animals limb and shipped back to the veterinarian. A separate unattached piece of neoprene is provided with the brace that the veterinarian must correctly trim for proper fitting. The neoprene is then tightly wrapped around the limb. The brace is placed over the neoprene with the idea that the neoprene prevents the brace from slipping. Strips of VELCRO are then tightly secured around the brace to compress the brace and hold it securely to the animals limb.

While custom made braces and splints address some of the fit problems presented by universal braces and splints, the delay between casting and fitting results in a period of time in which the animal can further injure itself or requires the added expense and inconvenience of temporary use of an alternate brace.

Another problem with existing animal limb braces and splints is the propensity for the brace or splint to slip or move. Various efforts have been made to solve this problem. Some braces and splints come equipped with an elaborate harness system. Others brace or splint beyond the affected area in an attempt to use other areas of the limb or body to hold the brace in place. Some use a "non-slip" material between the animals limb and the brace or splint. Some just accept the slippage as a matter of course.

Another problem with existing animal limb braces and splints is that the devices are normally made or designed to treat or support only one joint or one localized limb area when the entirety of the limb may need treatment or support. This then results in using various braces and/or splints that were not designed to be used in conjunction with each other and the treatment or support can be ineffective.

Another problem with existing animal limb braces and splints is the internal portion of the brace or splint that is adjacent the leg becomes dirty and riddled with bacteria thus presenting hygienic issues and in some instances, providing a vehicle for the introduction of infection to an incision area. Additionally, if the padding is not fitted correctly, the circulation of the limb is affected severely damaging the limb or paw.

Generally, existing animal limb braces and splints utilize strips of VELCRO or straps as the tightening and/or attachment method. This allows the brace or splint to be adjusted by pulling the VELCRO strap tighter or loosening it. However, a problem with this method is that it provides compression of the brace or splint only at the VELCRO/strap locations and causes a pressure point where the VELCRO strip/strap contacts the animals limb, resulting in inconsistent, uneven or undue pressure.

While significant advances have been made for human knee braces, it would not be suitable to modify a human knee brace to fit the stifle joint of an animal. The biomechanical forces of a human knee are much different than those of an animal. For example, the stance of the canine knee is different than the stance of the human knee. Humans stand upright, with their femur directly on top of their tibia, having a joint angle of 180°. Dogs stand with an angle of 135°. Thus, every time that a dog stands, the bone alignment is dependent upon an intact CCL to hold the bones in place in the stifle (knee) joint. Additionally, the actual structural dimensions of animal limbs vary significantly from that of humans. For example, the cross section of the upper thigh area of a human leg is substantially round while the cross section of the upper thigh area of a canine's rear leg is substantially oval. Thus, the forces acting on the leg from the contact points of the brace can be quite different.

There is also an overall variability in animal scale size among varying animal species and breeds that is significantly greater in animals than in humans. Thus, there is a greater variability in the circumference and length of animal limbs versus human legs.

In view of the shortcomings of known animal limb braces and splints, there is a demand for an orthopedic animal brace or splint which is simple to employ but capable of exerting distributed compression forces against the animal to effectively treat and stabilize the weakened limb, is customizable in size, and provides sufficient anatomical support capable of servicing a wide variety of anatomical contours and treatment levels.

SUMMARY OF THE INVENTION

Disclosed herein are various embodiments of orthoses for use on a limb of an animal that provide stability for unstable joints and limbs for short or long term support and function. These devices are designed to prevent the occurrence of, or reduce the severity of, a joint injury. These devices may be custom molded and fitted immediately after corrective surgery, or during a single visit to a veterinarian office, and can support and stabilize the joint while assisting or restricting the range of motion. In various embodiments, these devices are configured to be fully modular with components that are replaceable as well as individually customizable so as to treat a wide range of injuries. In various embodiments, these devices may be modular in configuration such that from one to all components can be used, customized or replaced as needed.

Various embodiments described herein include a rigid customizable brace that can be thermoformed to fit any part of a limb of an animal. Each thermoformed brace component may be linearly and/or circumferentially adjustable, lightweight, removable, reusable and waterproof. In various embodiments, the brace may include one or more modular brace components that each may be provided in different sizes with each brace member being replaceable and/or customizable. In various embodiments, multiple brace components can be interconnected using a hinge mechanism which can be locked, or set in one position, or have range of motion as desired. In various embodiments, a fastening/tightening system provides for consistent, even pressure forces along the limb. Some embodiments utilize a laced cord tightening system that provides for uniform tensioning at multiple points along the linear length of a brace component. Some embodiments of the fastening/tightening system may include the feature of a partly or fully detachable closure system which provides consistent, even pressure across and/or along a limb, and which can be coupled to the brace component as desired for a custom fit.

In one embodiment, the present invention comprises a brace having a single brace portion. Such a brace may be suitable to treat metatarsal injuries on the hind limb of an animal, or to treat metacarpal injuries on the front limb of an animal.

In another embodiment, the present invention comprises a brace configured with two separate individual brace portions, each portion connected by a rigid and/or hinged structure, as desired. Such a brace may be suitable to treat an Achilles injury on the hind limb of an animal, or to treat an elbow injury (subluxation) on the front limb of an animal.

In another embodiment, the present invention comprises a brace configured with three separate individual brace portions, each portion connected by a rigid and/or hinged structure, as necessary. Such a brace may be suitable to treat cranial cruciate ligament injuries on the hind limb of an animal.

Various embodiments described herein may also include a paw cover that can be formed to fit the paw of an animal and is able to be incorporated into, or coupled with, the brace or splint.

According to various embodiments, the present invention may be suitable for short-term stabilization of a limb of an animal. According to various embodiments, the present invention may be suitable for long-term stabilization of a limb of an animal. According to various embodiments, the present invention may be suitable for prophylactic usage prior to surgery to prevent further injury. According to various embodiments, the present invention may be suitable for immediate immobilization and/or stabilization of a limb after surgery. According to various embodiments, the present invention may be suitable for usage during rehabilitation, including rehabilitative exercises in water.

BRIEF DESCRIPTION OF THE DRAWINGS

The invention may be more completely understood in consideration of the following detailed description of various embodiments of the invention in connection with the accompanying drawings, in which:

FIG. 3a is a top view of a brace stabilization bar system and hinge where the individual openings are spaced longitudinally along the stabilization bars.

FIG. 3b is a side view which shows the elevation of a flat stabilization bar and hinge system.

FIG. 4 is a cross sectional view of a cover over the mechanical reel.

FIG. 12 is a top plan view of an embodiment of the tensioning system using a mechanical reel and a plurality of hook and loop wings.

FIG. 13 is a front view of the semi-customizable animal orthopedic splint type brace having a first splint component and an attached closure system.

FIG. 16 is a front view of a paw cover.

FIG. 17 is a rear view of a paw cover.

Figure 1:
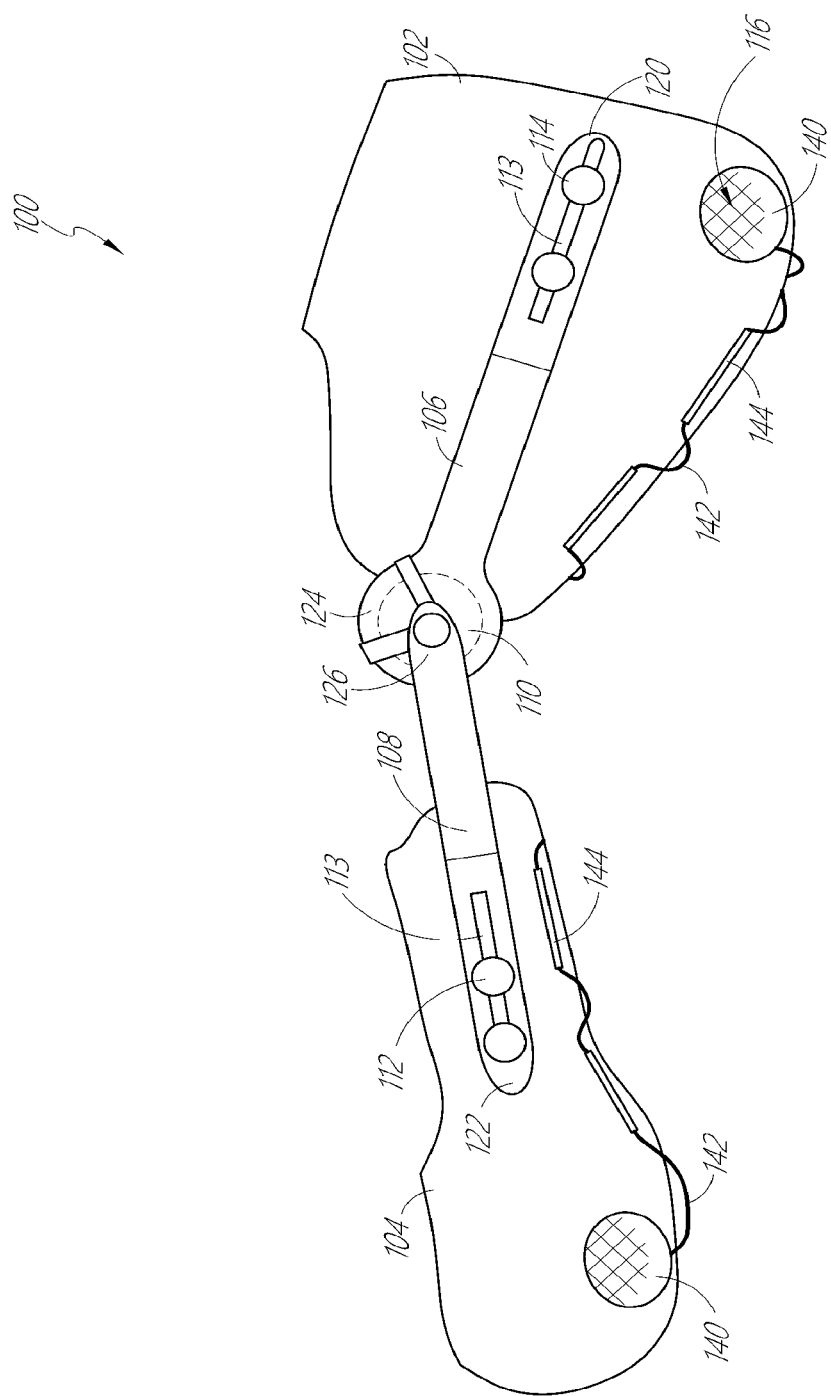
FIG. 1 is a side view of the animal orthopedic brace designed for the stifle joint of a canine.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE DRAWINGS

The following detailed description should be read with reference to the drawings in which similar elements in different drawings are numbered the same. The drawings, which are not necessarily to scale, depict illustrative embodiments and are not intended to limit the scope of the invention.

Figure 2:
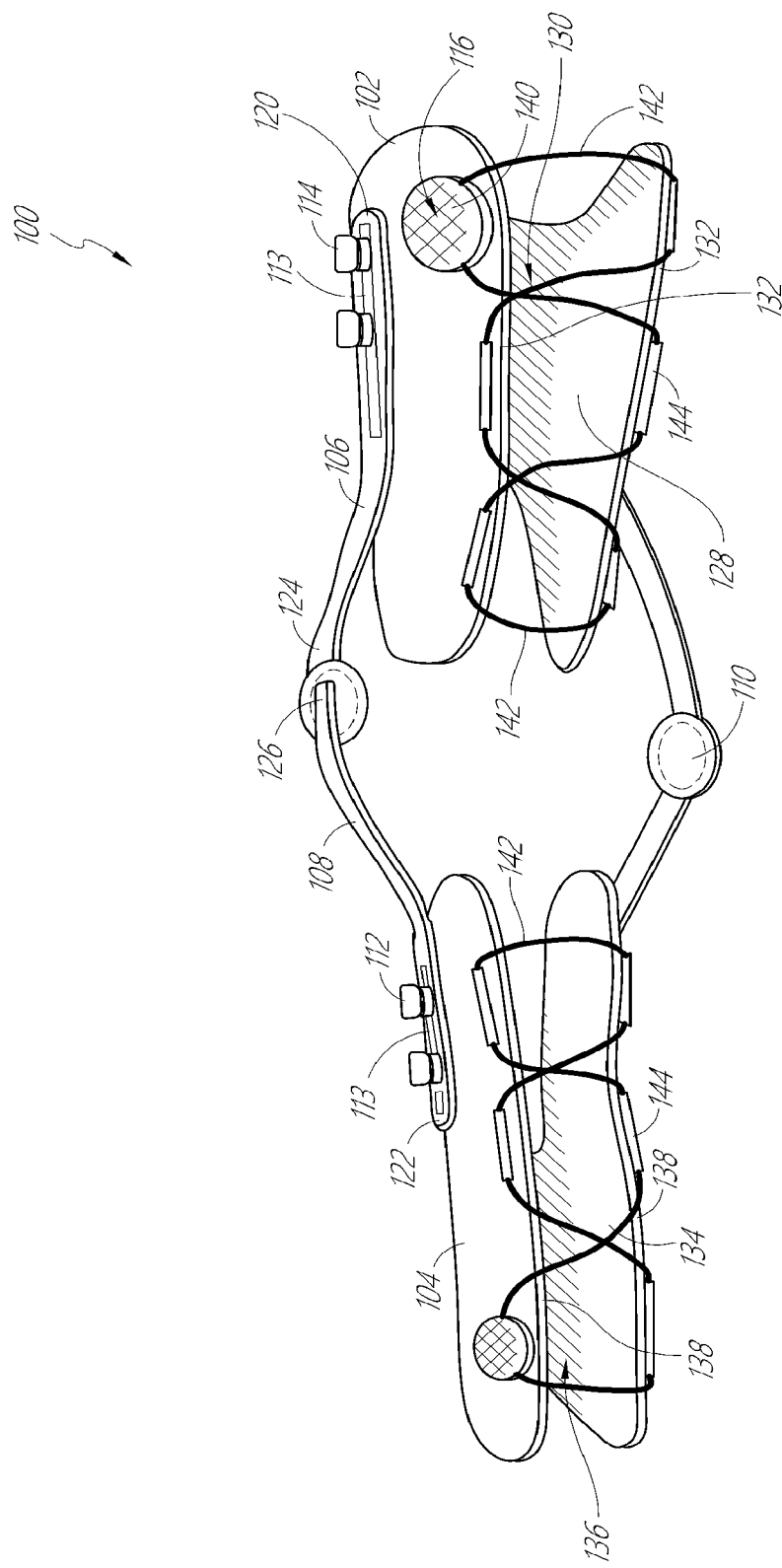
FIG. 2 is a front or anterior view of the animal orthopedic brace designed for the stifle joint of a canine.

Embodiments of the present invention include various arrangements of orthopedic braces and splints for supporting or immobilizing one or more limbs of an animal. The braces and splints may be configured to treat injuries on a front limb or on a rear limb, FIGS. 1 and 2 depict an embodiment of an animal orthopedic brace configured to support and stabilize the stifle joint of a canine. Components of the brace 100 include a customizable femur component 102, a customizable tibia component 104, an upper stabilization bar 106, a lower stabilization bar 108, a hinge 110, lower adjustment screws 112, upper adjustment screws 114, and a closure system 116.

Figure 2A:
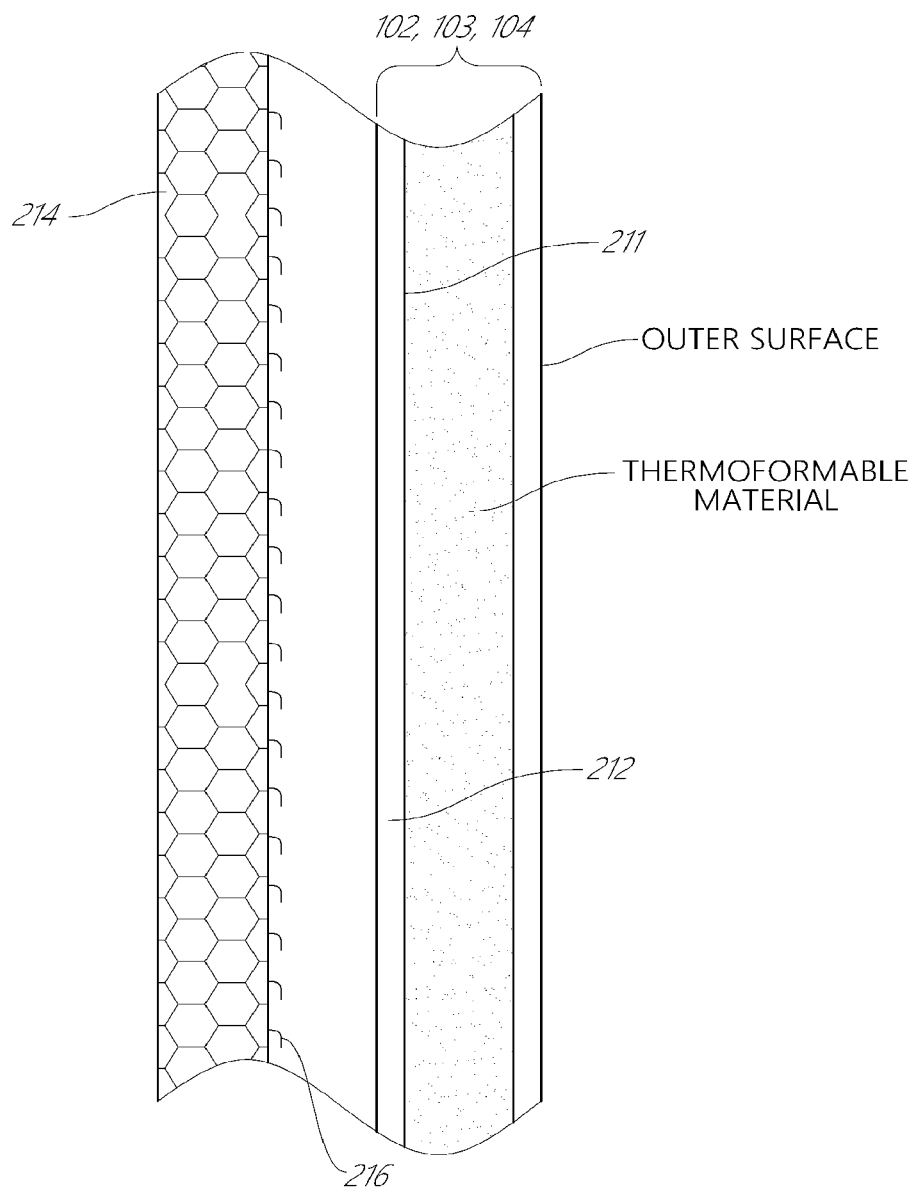
FIG. 2a is a cross sectional view of the replaceable open cell foam provided for the inner surface of the brace components.
Figure 2B:
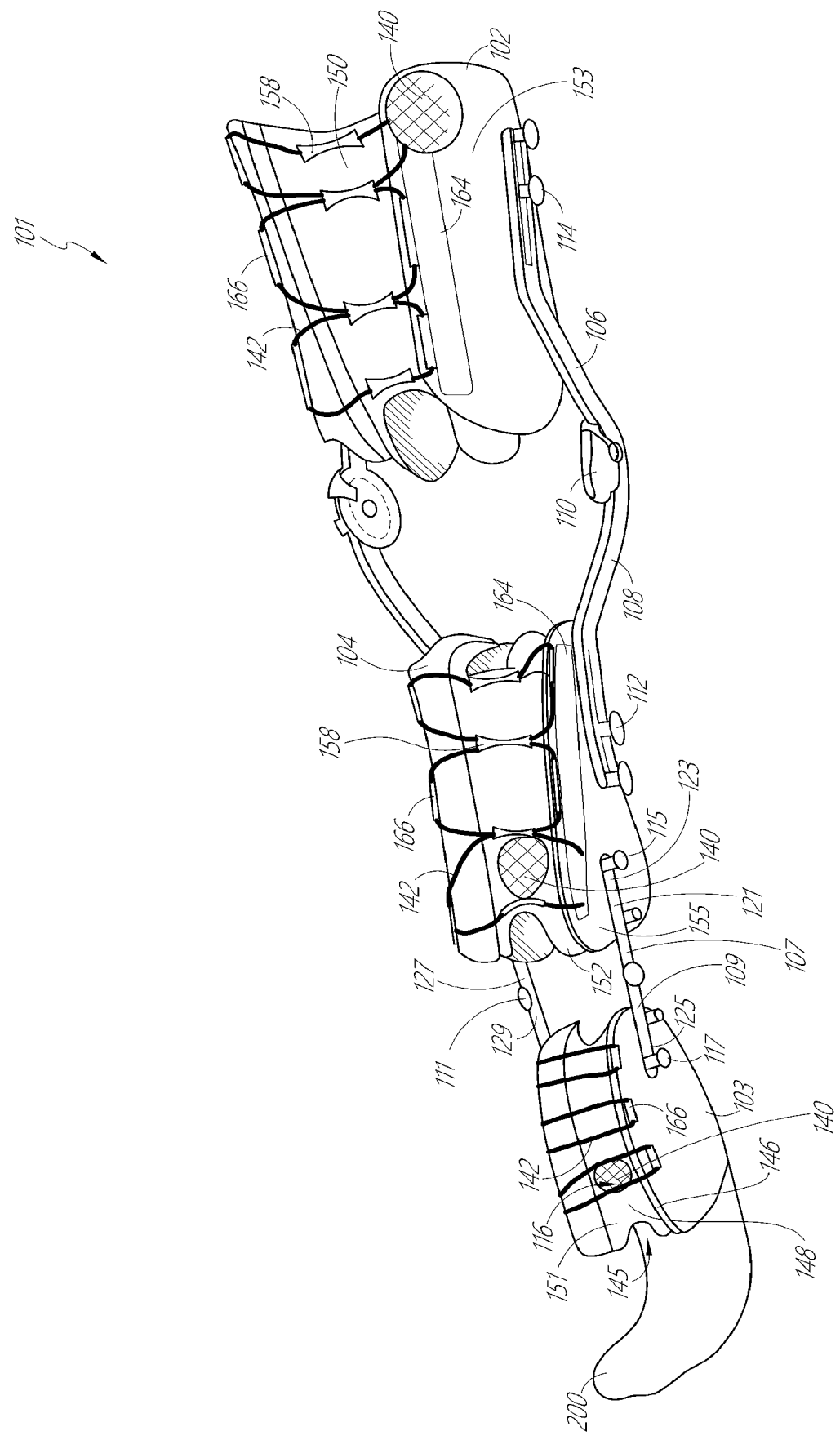
FIG. 2b is a front or anterior view of the animal orthopedic brace incorporating a sub-hock component and a body closure system.
Figure 2C:
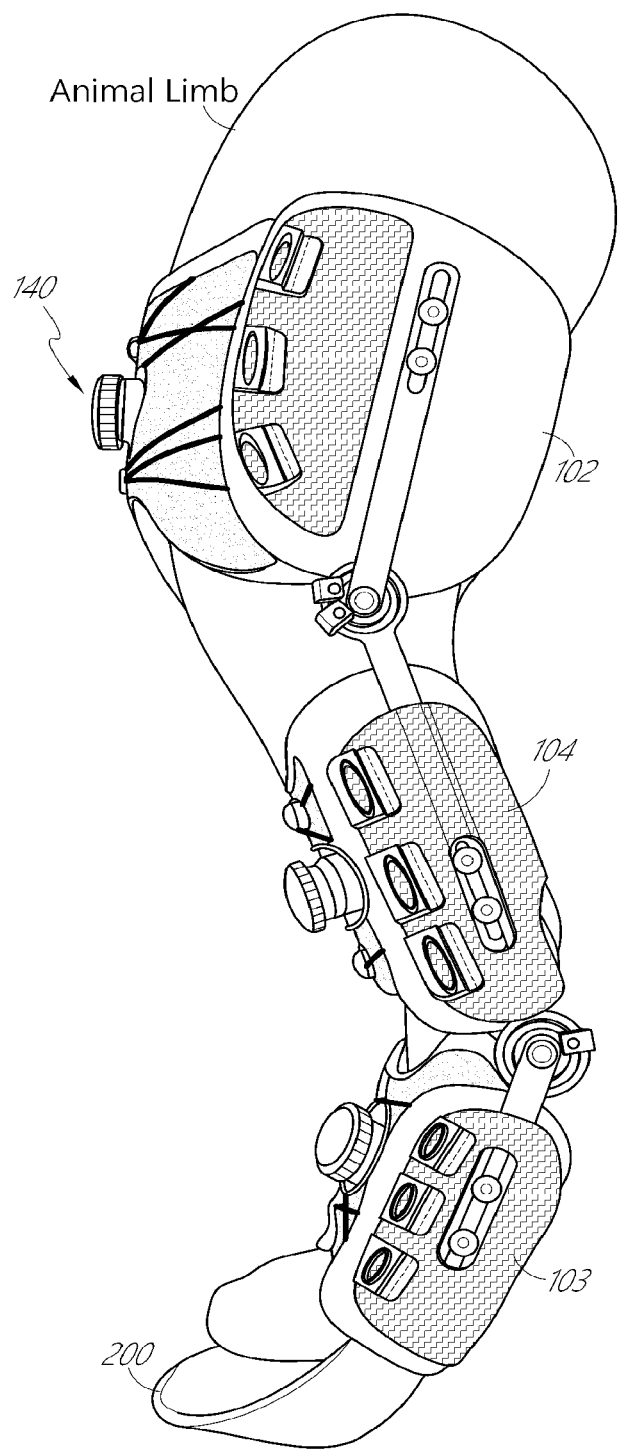
FIG. 2c is a side view of an alternate embodiment of the brace of FIG. 2b.
Figure 2D:
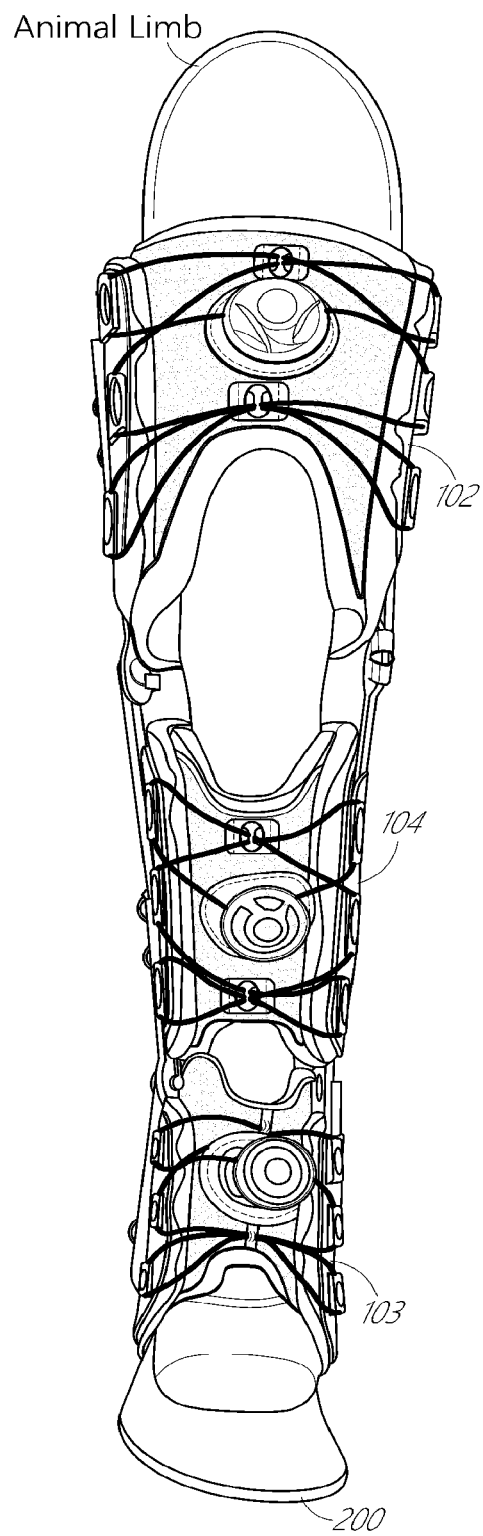
FIG. 2d is a front view of the brace of FIG. 2c.

FIG. 2b depicts another embodiment of an animal orthopedic brace configured to support and stabilize the stifle joint in conjunction with supporting and stabilizing the hock of a canine. Components of the brace 101 include the same features as the brace depicted in FIGS. 1 and 2 but additionally feature a semi-customizable hock component 103, a secondary upper stabilization bar 107, a secondary lower stabilization bar 109, a secondary hinge 111, secondary lower adjustment screws 117, secondary upper adjustment screws 115, and a closure system 116. The brace 101 can also feature an optional paw cover 200.

It is contemplated that the brace 100, 101 is fully modular and each component listed above is swappable/replaceable so that various sizes and configurations can be adjoined to properly size the orthosis to the limb of the animal. For example, a reduction in the swelling of the upper thigh could result in improper compression of the femur component 102. Thus, the femur component 102 can be replaced with a femur component 102 of a different size while retaining all other components including the tibia component 104, the upper stabilization bar 106, the lower stabilization bar 108, the hinge 110, the lower adjustment screws 112, the upper adjustment screws 114, and the closure system 116. Another example would be of a long-legged animal where the upper and lower stabilization bars 106, 108 can be swapped with bars of a different length to be length appropriate. Another example is a damaged component that will not function as designed, e.g. a closure system 116 that has been chewed by the animal. The component, in this case the closure system 116, is easily removed and replaced with a fully functional component while retaining all of the other original components.

According to various embodiments, the braces described herein are configured to be modular, such that femur component 102 may be used individually, or may alternately be configured to be used in conjunction with a tibia component 104 with the use of stabilization bars 106, 108.

One advantage of a fully modular system is that the entire brace 100, 101 is not required to be replaced resulting in a cost savings to the owner of the animal. Another advantage is that all components can be sized and properly fitted to the needs of the animal whereas current bracing systems that do not provide modularity may fit one area of a limb properly while allowing another area to float. Another advantage is that where the entirety of the limb may need treatment or support, the brace 100, 101 is specifically made and designed to treat or support the entire limb thus providing effective treatment and support.

The brace 100, 101 can be applied as a prophylactic device to prevent or reduce the severity of a joint injury, as a rehabilitative device to support and stabilize a joint while assisting or restricting range or motion, or as a functional device to provide stability for chronically unstable joints and limbs for long term support and function. The customized formation of the femur component 102, the tibia component 104 and the hock component 103 along with the proper placement of the stabilization bars 106, 107, 108, 109 provide stabilization in which the brace 100, 101 maintains proper alignment of the joints in relation to the rest of the limb while providing support to the joints so that the biomechanical forces of the animal joint are as natural as possible.

The customizable femur component 102 and the customizable tibia component 104 are made of a lightweight composite material including at least one layer of thermoformable material, and are designed to substantially encompass the circumference of the limb. In one embodiment, the composite material is of the type described in U.S. Published Patent Application No. 2012/01011417 to Joseph, or in U.S. Pat. No. 8,303,527 to Joseph, the disclosures of which are hereby incorporated by reference in their entireties. As described therein, the composite material generally includes an inner foam layer for comfort, a middle thermoformable polymer material, and an outer layer of durable fabric. In some embodiments, the thermoformable polymer material may be thermoformable within a target temperature range of 150-320 degrees Fahrenheit, or within a target temperature range of 160-240 degrees Fahrenheit, or within a target temperature range of 180-225 degrees Fahrenheit. In some embodiments, the thermoformable polymer material is substantially rigid at temperatures below a minimum formable temperature of about 150 degrees Fahrenheit, or below about 140 degrees Fahrenheit, or below about 130 degrees Fahrenheit. In some embodiments, the thermoformable polymer material may have a dwell time of about three to ten minutes, or of about five to eight minutes. In some embodiments, the outer layer can be manufactured of an unbroken loop fabric which complements the hook fabric in a hook and loop type fastener. In another embodiment, components 102, 104 are constructed of a material such as described in U.S. patent application Ser. No. 13/836,660 to Joseph, filed Mar. 15, 2013 and titled "Foam Core Sandwich Splint," the disclosure of which is incorporated by reference.

In alternate embodiments, the inner surface 181 of the brace component is comprised of an unbroken loop fabric 182 and does not include an incorporated inner foam layer (as noted above) but can instead be provided with a separate open cell foam sheet 184, as illustrated in FIG. 2a. One side of the open cell foam sheet is provided with the hook portion 186 of a hook and loop material, the hook portion 186 complementing the unbroken loop fabric 182 covering the inner surface of the component. Thus, the open cell foam sheet 184 is adherently attached to the inner surface of the component and can be easily removed and replaced. The open cell foam sheet 184 can be provided with an antimicrobial treatment to reduce the chance of bacterial infections. One advantage of the replaceable open cell foam sheet 184 is that the foam layer can be replaced without the need to replace the entire component resulting in cost savings and extending the life of the component. The open cell foam also has the advantage of being provided in different thicknesses, and also in varying thicknesses of the same sheet, thus providing varying levels of cushioning or breathability as needed. It should be noted that this embodiment is equally adaptable and able to be incorporated in all embodiments as described below in this detailed description.

The femur component 102 and tibia component 104 can be provided to a veterinarian as part of a kit that includes substantially flat (planar) sheets of shaped material or somewhat pre-formed into a general u-shape. The veterinarian heats the components 102, 104, generally using a dry heat source, making the material malleable and able to be custom shaped, in the veterinarian's office, to the animals limb. Heating can be accomplished using, for example, ovens, convection ovens, radiant lamp heat sources, infrared heaters, microwave ovens, self heating pouches, internal heating system built into the material, or exothermic heating source. In addition, wet heat can be used, for example, immersion of the material into hot water.

While the material is hot and malleable, the veterinarian places the material on the appropriate area of the animal's limb and forms the material around the limb to obtain a precise custom fit. As the material cools, the material becomes rigid and retains the shape of the limb. An advantage of using this lightweight composite material is that the components 102, 104 can be molded and custom fitted in the veterinarian's office without the need to make a casting or send the components 102, 104 to an outside laboratory. Another advantage is that due to the dry heating methods the brace can be applied immediately after surgery versus a cast or other brace that may require wetting in order to form it thus introducing moisture to the incision area.

In one embodiment, the femur component 102 is molded to the upper thigh area of a canine's hind leg. The veterinarian chooses the material based on the size of the animal so that the material, when formed, fits substantially around the circumference of the upper thigh leaving a longitudinal opening 128 at the front or anterior of the leg. Thus, when formed, the femur component 102 forms a substantially u-shaped channel 130, as shown in FIG. 2, where the ends 132 of the u-shaped channel 130 do not touch. The opening 128 allows for easy placement and removal of the femur component 102 since the ends 132 of the u-shaped channel 130, though rigid, can be easily spread apart in order to place the canine's upper thigh into the u-shaped channel 130 between the ends 132 of the u-shaped channel 130. In an alternate embodiment, the component 102 can be formed such that the longitudinal opening 128 can be located at the posterior or rear of the leg.

In another embodiment, the femur component 102 is molded so that the ends 132 of the u-shaped channel 130 overlap when formed to the canine's upper thigh.

The tibia component 104 is molded to the lower thigh area of the canine's hind leg. The veterinarian chooses the material based on the size of the animal so that the material, when formed, fits substantially around the circumference of the lower thigh leaving a longitudinal opening 134 at the front or anterior of the leg. Thus, when formed, the tibia component 104 forms a substantially u-shaped channel 136, as shown in FIG. 2, where the ends 138 of the u-shaped channel 136 do not touch. The opening 134 allows for easy placement and removal of the tibia component 104 since the ends 138 of the u-shaped channel 136, though rigid, can be easily spread apart in order to place the canine's lower thigh into the u-shaped channel 136 between the ends 138 of the u-shaped channel 136. In an alternate embodiment, the component 104 can be formed such that the longitudinal opening 134 can be located at the posterior or rear of the leg.

In another embodiment, the tibia component 104 is molded so that the ends 138 of the u-shaped channel 136 overlap when formed to the canine's lower thigh.

While the above was described in relation to the stifle joint of a canine, it is understood that the process is applicable to the forelimb or rear limb of any animal. It is also contemplated that the femur component 102 and the tibia component 104 can be used in conjunction with each other or alone.

As shown in FIGS. 1 and 2, an external frame provides connectivity between the femur component 102 and the tibia component 104. The external frame has an upper stabilization bar 106 attached to the femur component 102 and a lower stabilization bar 108 attached to the tibia component 104. The stabilization bars 106, 108 can be designed to be linearly adjustable in relation to the femur component 102 and the tibia component 104. That is, the linear adjustment is in the longitudinal direction of the limbs. Alternatively, the stabilization bars 106, 108 can be designed to be non-adjustable in relation to the femur component 102 and the tibia component 104. Attachment of the stabilization bars 106, 108 to the components 102, 104 can be made as shown in the embodiment of FIGS. 1 and 2 with the use of adjustment screws 112, 114 and threaded receivers that are molded into, combined with, or otherwise engaged with the lightweight composite material. Separate receivers may be provided for each of screws 112, 114, or a single receiver may be provided to receive both of screws 112, 114. Other embodiments contemplate other methods of attaching the stabilization bars 106, 108 to the components 102, 104 including other known fasteners such as nuts, bolts, rivets, pins, retaining rings, clips, etc. Other embodiments contemplate that attachment of the stabilization bar 106, 108 to the lightweight composite material of the femur component 102 or tibia component 104 can be made by the use of crimping, gluing, soldering, cementing, adhesives, etc. or incorporation of the stabilization bar 106, 108 into the lightweight composite material of the femur component 102 or tibia component 104.

One embodiment provides that the upper stabilization bar 106 and lower stabilization bar 108 are linearly adjustable in relation to the components 102, 104. The stabilization bars 106, 108 are provided with bar adjustment slots 113 at their distal ends 120, 122. The slots 113 are sized to be smaller than the head of the adjustment screws 112, 114 so that tightening of the screws 112, 114 cause the heads to compress the stabilization bars 106, 108 against the components 102, 104 preventing the stabilization bars 106, 108 from moving in relation to the components 102, 104. In the embodiment illustrated, the adjustment screws 112, 114 are thumbscrews but they can be any type of fastener that can be tightened including, wingnuts, nuts, ratchets, screws, etc.

Other embodiments, as illustrated in FIG. 3, can incorporate separate openings 118 that are evenly spaced longitudinally along the stabilization bars 106, 108. The openings can be sized to accept pins, screws, push-button adjustments, etc. The openings can be any shape including round, square, triangular, etc.

In one embodiment, a tuberosity strap is provided as part of the present invention, and may be separate from, or coupled to a portion of the orthopedic brace and/or the external frame.

The proximal end 124 of the upper stabilization bar 106 engages with the proximal end 126 of the lower stabilization bar 108 and forms an orthopedic hinge assembly 110. The hinge assembly 110 maintains the animal joint in a biomechanically natural state to support the joint while restraining the joint from harmful motions. In one embodiment, the hinge assembly 110 can be a full range of motion (ROM) hinge maintaining selective ranges of flexion and extension. Other embodiments can incorporate other hinges known in the art, for example, single pivot hinges, dual pivot hinges, and veterinary TAMARACK FLEXURE JOINTS®. The hinge assembly 110 can be designed so that it can be used in a locked position preventing any rotation or unlocked allowing limited to full rotation.

The upper stabilization bar 106 and lower stabilization bar 108 can be configured so that the profile of the stabilization bars 106, 108 follow the contours of the animal's leg, as illustrated in FIG. 2. An alternate embodiment, shown in FIG. 3a, allows for the upper stabilization bar 106 and lower stabilization bar 108 to be substantially flat. It is contemplated that alternate configurations of upper stabilization bar 106 and lower stabilization bar 108 can be incorporated, e.g., a contoured upper stabilization bar 106 paired with a flat lower stabilization bar 108 or vice versa.

The brace 100 includes a closure system 116 having a mechanical reel 140 and lace 142 to provide smooth, uniform closure of the brace 100 with little or no pressure points. Reel 140 comprises a tightening mechanism, and is preferably of the type available from Boa Technology, such as described in U.S. Pat. Nos. 5,934,599, 6,202,953, 6,289,558, 7,950,112, 7,954,204, 7,992,261, 8,091,182, and 8,277,401, the disclosures of which are incorporated by reference herein. Alternatively, other fastening mechanisms such as cord locks, cam cord locks, traditional lacing bows, ratchet lace systems, or other lacing or cabling methods may be used in place of any of the closure systems described herein.

At least one closure system 116 can be provided for the femur component 102 and at least one closure system 116 can be provided for the tibia component 104. The mechanical reel 140 is attached to the appropriate component 102, 104 at a convenient location. There are no restrictions as to where the mechanical reel can be attached as long as the lace 142 and the reel 140 are not impeded by other structures on the component 102, 104. In one embodiment, the reel 140 is located on the posterior side of the component 102, 104. In another embodiment, the reel 140 is located on the side of the component 102, 104.

The mechanical reel allows for the lace 142 to be drawn in and tightened by turning the mechanical reel 140. The mechanical wheel 140 allows for precise tightening of the lace 142 in order to fine tune, and then lock in, the amount of compression provided to the leg by the brace 100. The lace 142 can be, for example, steel, nylon or other non-stretchable material. A lace 142 constructed of steel or other suitable metal provides superior resistance to chewing by the animal during the duration of wearing brace 100. The lace 142 is threaded through guides 144 that are molded into or otherwise engaged with the lightweight composite material. In one embodiment, the guides 144 are a plurality of nylon sleeves or loops. In another embodiment, the guides 144 can be made of the lightweight composite material, plastic, metal or another suitable material and form a protrusion having an aperture that the lace 142 is threaded through. The guides 144 are placed longitudinally along the component 102, 104 so that they are substantially parallel to each other on either side of the u-shaped channel 130, 136. Alternately, guides 144 may be coupled to or otherwise included as one-half of a clip or buckle arrangement, wherein the other half of the clip or buckle is secured to brace 100. The closure system 116 allows for adjustability, to a micro level, to allow adjustment after initial fitment such as to accommodate swelling and/or atrophy.

The mechanical wheel 140 can be designed so that its low profile or material resists chewing. In another embodiment, the mechanical wheel 140 can be covered with a cover 141 as is depicted in FIG. 4. The cover 141, as shown, may comprise a conical shape, and is configured to completely cover the mechanical reel 140. Openings (not shown) are provided at the outer edges of cover 141 allowing the laces 142 to pass through unimpeded. The cover 141 can be manufactured from plastic or metal so long as the profile of cover 141 is such that an animal biting at the cover could not grip the cover between its teeth. In other embodiments, the cover 141 can be a pyramid, or a partial spherical or ovoid shape.

Figure 5:
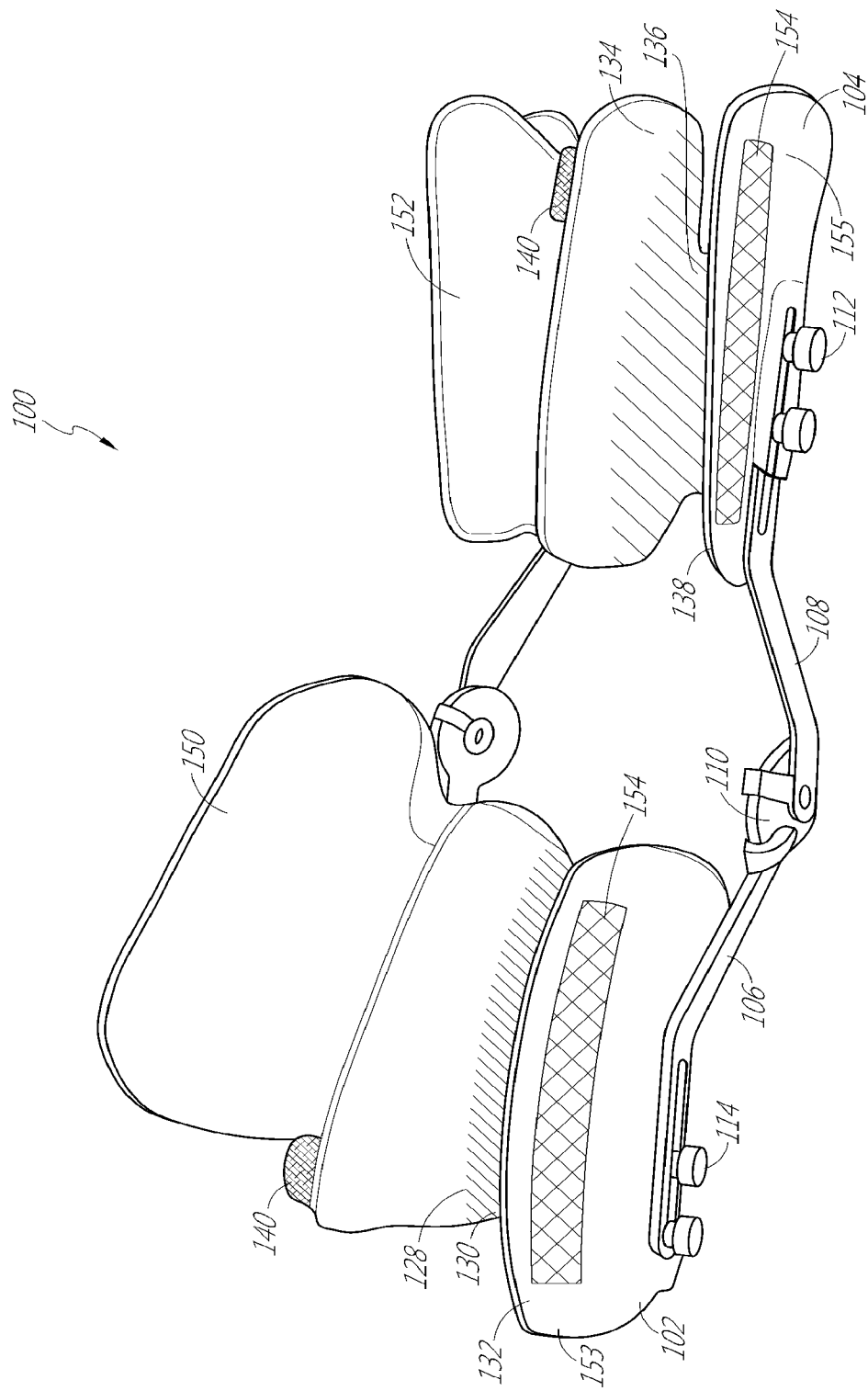
FIG. 5 is a front view of the animal orthopedic brace designed for the stifle joint of a canine incorporating a closure system in the open position.
Figure 6:
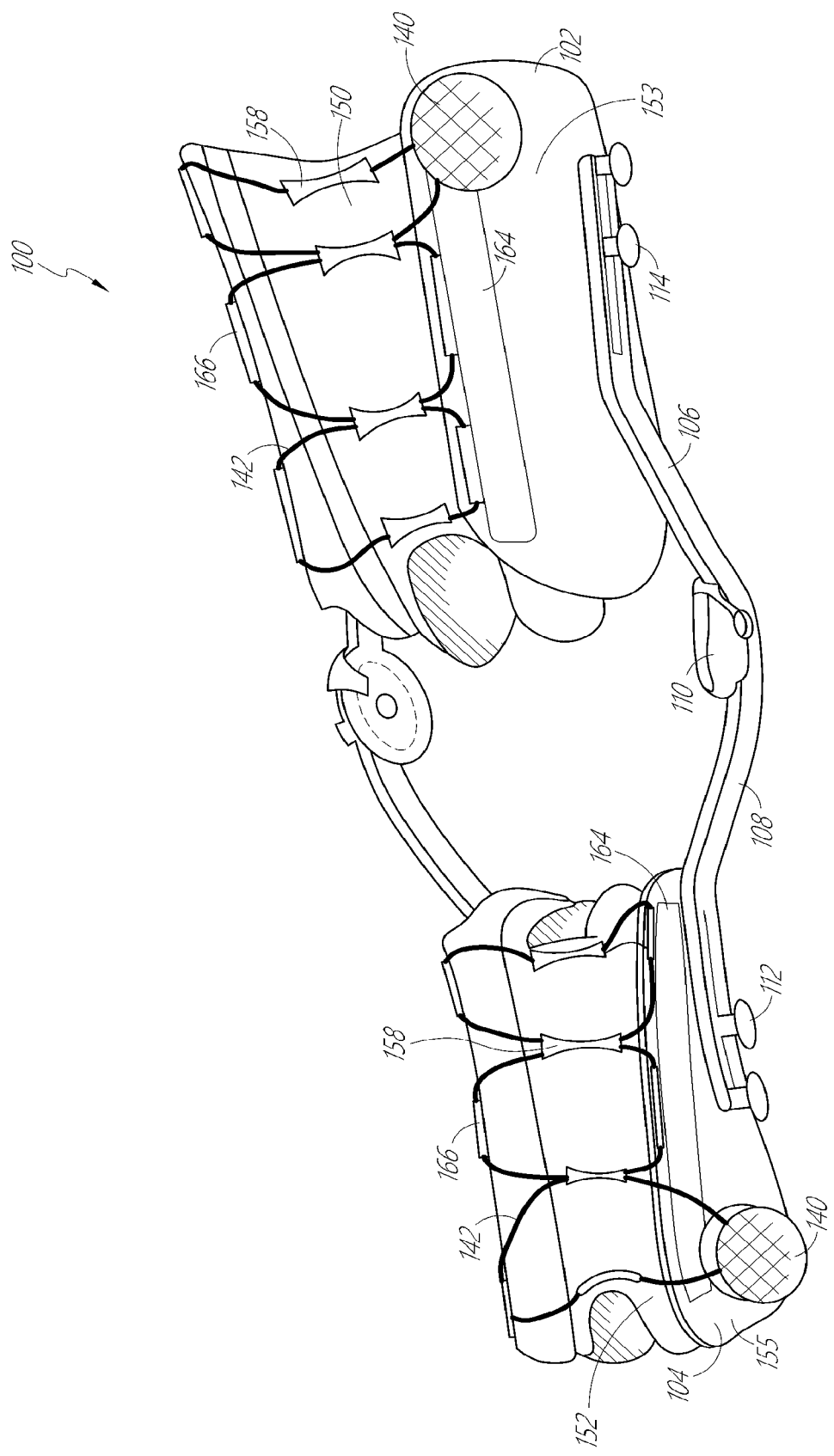
FIG. 6 is a front view of the animal orthopedic brace designed for the stifle joint of a canine incorporating a closure system in the closed position.

FIGS. 5 and 6 depict another embodiment of an animal orthopedic brace configured to support and stabilize the stifle joint of a canine. Where the features of this embodiment are comparable to the features of FIGS. 1 and 2, the same reference numbers will be used. In addition, for the sake of brevity, description is only provided for those features of this embodiment that are not provided in the embodiment as shown in FIGS. 1 and 2.

As depicted in FIGS. 5 and 6, components of this embodiment of the brace 100 include a customizable femur component 102, a customizable tibia component 104, an upper stabilization bar 106, a lower stabilization bar 108, a hinge 110, lower adjustment screws 112, upper adjustment screws 114, a femur closure body system 150 and a tibia closure body system 152. It is contemplated that the femur component 102 and the tibia component 104 can be used in conjunction with each other or alone.

As similarly described above, the customizable femur component 102 and the customizable tibia component 104 are each made of a lightweight composite material including an inner foam layer for comfort, a middle thermoformable polymer material, and an outer layer of durable fabric. In some embodiments, the outer layer can be manufactured of an unbroken loop fabric which complements the hook fabric in a hook and loop type fastener. The customizable femur component 102 and the customizable tibia component 104 are each designed to substantially encompass the circumference of the limb.

The femur component 102 is heated and molded to the upper thigh area of the canine's hind leg so it fits substantially around the circumference of the upper thigh leaving a longitudinal opening 128 at the front or anterior of the leg or alternately, at the rear or posterior of the leg. Thus, when formed, the femur component 102 forms a substantially u-shaped channel 130, as depicted in FIG. 5, where the ends 132 of the u-shaped channel 130 do not touch. In another embodiment, at least one side of the outer surface 153 of the femur component 102 is provided with the loop portion of a hook and loop closure 154 (e.g. VELCRO® Brand hook and loop closures) along its length. In another embodiment, both outer surfaces 153 of the femur component 102 are provided with the loop portion of a hook and loop closure 154 along their lengths.

The tibia component 104 is heated and molded to the lower thigh area of the canine's rear leg so it fits substantially around the circumference of the lower thigh leaving a longitudinal opening 134 at the front or anterior of the leg or alternately, at the rear or posterior of the leg. Thus, when formed, the tibia component 104 forms a substantially u-shaped channel 136, as depicted in FIG. 3, where the ends 138 of the u-shaped channel 136 do not touch. In another embodiment, at least one side of the outer surface 155 of the tibia component 104 is provided with the loop portion of a hook and loop closure 154 (e.g. VELCRO brand hook and loop closures) along at least a substantial portion of its length. In another embodiment, both outer surfaces 155 of the tibia component 104 are provided with the loop portion of a hook and loop closure 154 along their lengths.

Figure 7:
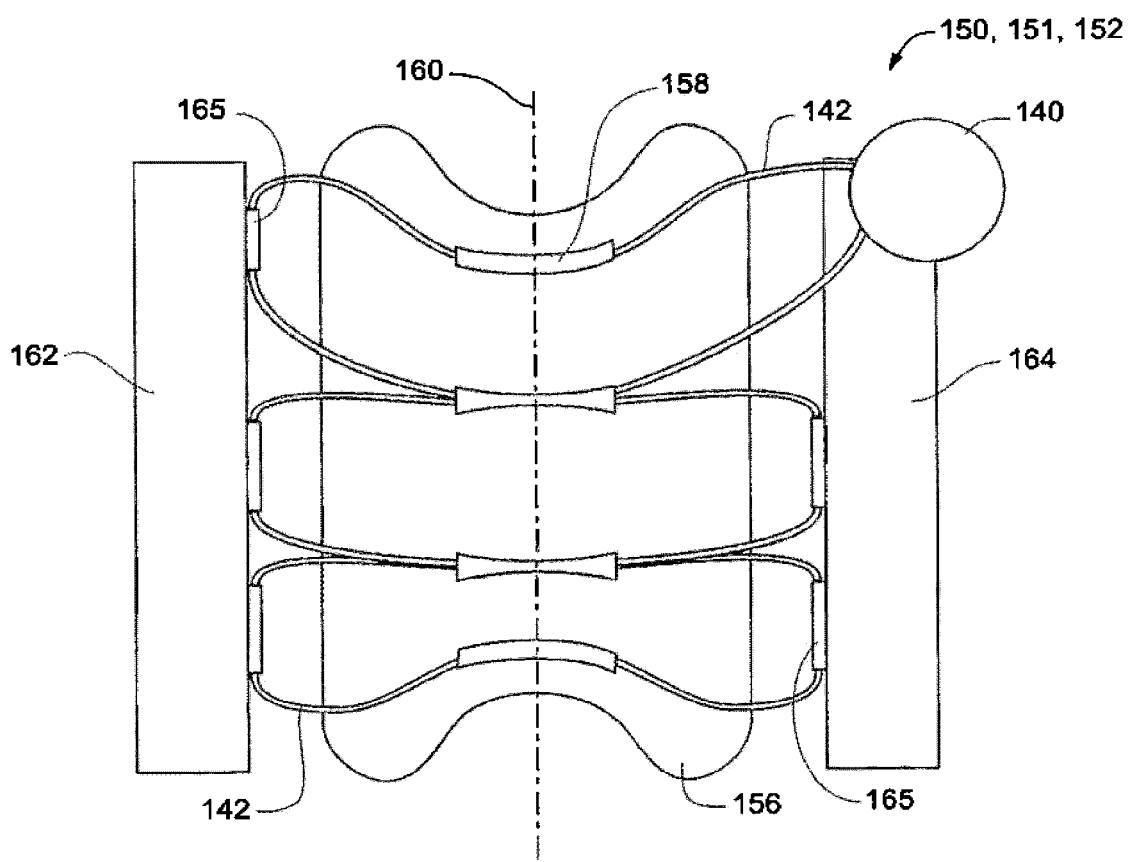
FIG. 7 is a top plan view of the closure system for an animal orthopedic brace.

The brace 100 is provided with a femur closure body system 150 and a tibia closure body system 152, as detailed in FIG. 7. The closure body 156 of the closure body system 150, 152 can be made of the same lightweight composite material as the component 102, 104 and is heated and subsequently formed to the appropriate portion of the animals limb. Alternatively, the closure body 156 can be provided so that it has a preformed u-shaped channel along its length. Alternatively, the closure body 156 can be made of another flexible material that can be shaped. The closure body 156 is sized so that when placed on the limb of the animal, it fits partially around the circumference of the animals limb. As illustrated, a plurality of guides 158 are located on the closure body 156 and are substantially perpendicular to the longitudinal axis 160 of the closure body 156. The profile of one or more of body 156, components 102, 103 and 104 may include reliefs or cutouts to provide clearance around joints, as depicted in FIGS. 2b-2d, and 5-7.

Figure 8:
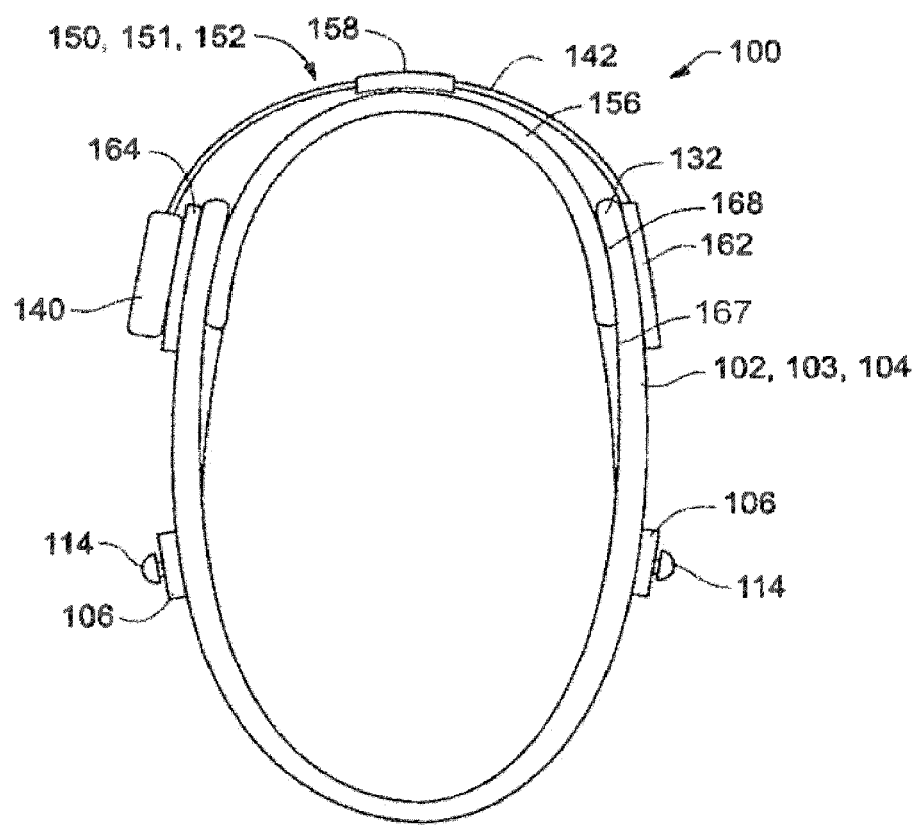
FIG. 8 is a cross sectional view of the animal orthopedic brace incorporating a closure system in the closed position.
Figure 9:
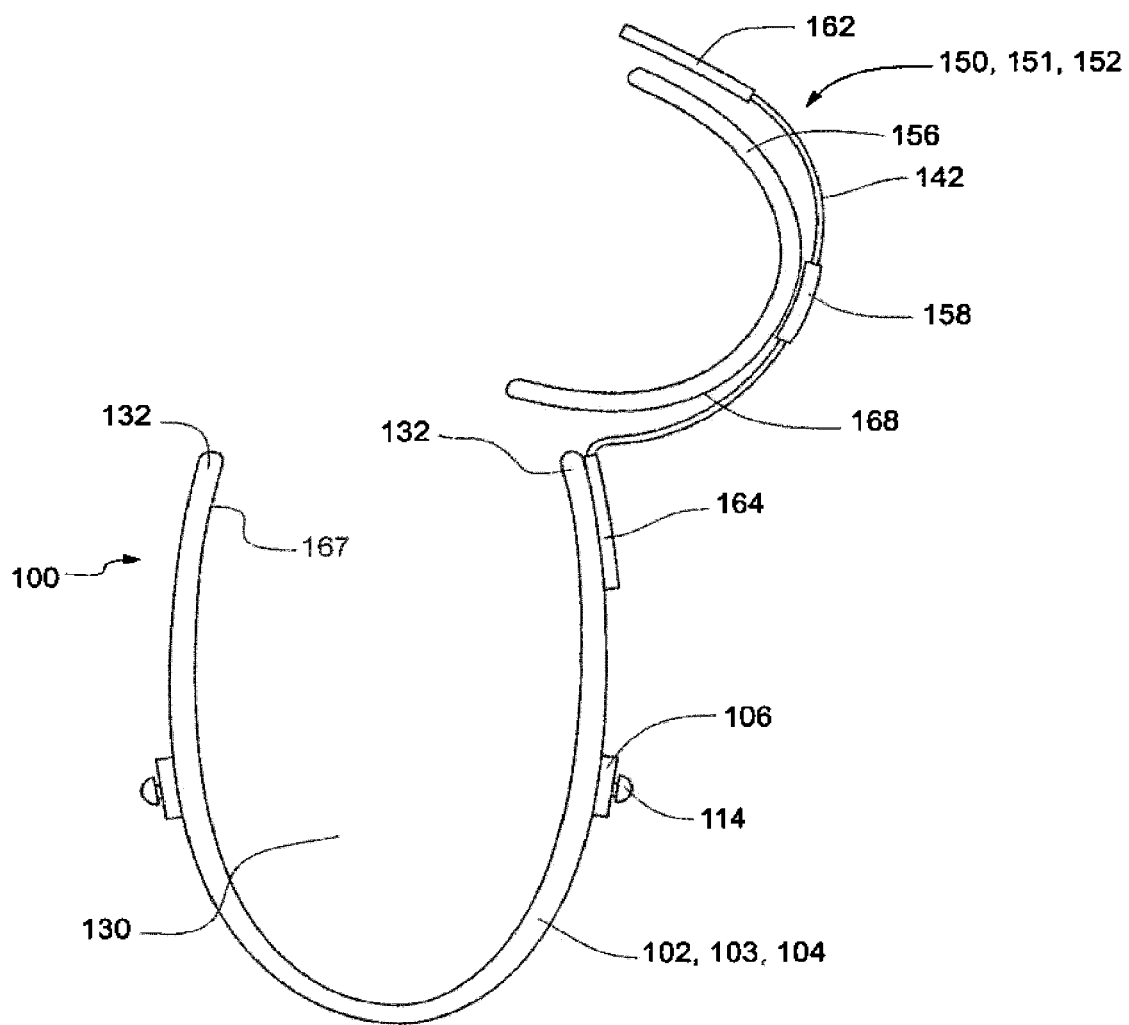
FIG. 9 is a cross sectional view of the animal orthopedic brace incorporating a closure system in the open position.

FIGS. 8 and 9 illustrate the component 102, 104 having a closure system 150, 152 in the closed and open positions, respectively. As illustrated in FIG. 8, when closed, the closure body 156 preferably sits on the animals limb so that when the component 102, 104 is positioned, the ends 132, 138 of the u-shaped channel 130, 136 overlap the closure body 156 sandwiching the closure body 156 between the ends 132, 138 of the u-shaped channel 130, 136 and the animals limb. Thus, the outer surface 168 of the closure body 156 slidably engages with the inner surface 166 of the component 102, 104.

The closure system 150, 152 has a first wing 162 made from the hook portion of a hook and loop woven material and a second wing 164 made from either woven material or the hook portion of a hook and loop woven material. Alternatively, more than two wings can be provided. The wings 162, 164 are provided with a plurality of guides 165 that are placed linearly along the length of the wings 162, 164 either on the edge of the wing 162, 164 or on the topside of the wing 162, 164. In one embodiment, the guides 165 are a plurality of nylon sleeves. In another embodiment, the guides 165 are a plurality of loops made from a woven material.

The hook material of the bottom side of the first wing 162 complements the unbroken loop fabric covering the brace. In another embodiment, the hook material of the bottom side of the first wing 162 complements the loop portion of the hook and loop closure 154 provided on the at least one outer side 153, 155 of the component 102, 104 thereby providing adhesion with the material on the at least one outer side 153, 155 of the component 102, 104. Thus, the wing 162 is adhered with the component 102, 104 surface opposite that of the animals limb. One advantage in providing a hook and loop closure is that the closure system 150, 152 can be detached from at least one side of the component 102, 104 allowing for easy insertion or removal of the animals limb into or out of the component 102, 104.

The second wing 164 can be made of a woven material. As depicted in FIG. 9, the woven material of the second wing 164 can be fixedly attached to the outer side 153, 155 of the component 102, 104 so that the wing 164 is on the component 102, 104 surface opposite that of the animals limb. Attachment can be by any manner that permanently attaches the woven material to the component 102, 104, for example, by adhesives, sewing, rivets, etc. Alternatively, the second wing 164 can be comprised of the hook of the hook and loop woven material and can be detachably connected to the unbroken loop fabric covering the component 102, 104 surface. In another embodiment, the hook provides adhesion to the loop portion of a hook and loop closure 154 provided on the at least one outer side 153, 155 of the component 102, 104 so that the wing 164 adheres with the component 102, 104 surface opposite that of the animals limb.

The closure body system 150, 152 further comprises a closure system 116 having a mechanical reel 140 and lace 142 to provide smooth, even closure of the brace 100 with no pressure points. Reel 140 is preferably of the type available from Boa Technology, such as described in U.S. Pat. Nos. 5,934,599, 6,202,953, 6,289,558, 7,950,112, 7,954,204, 7,992,261, and 8,091,182, the disclosures of which are incorporated by reference herein. Alternatively, other fastening mechanisms such as cord locks, cam cord locks, traditional lacing bows, ratchet lace systems, or other lacing methods may be used in place of any of the closure systems described herein.

At least one closure body system 150, 152 can be provided for the femur component 102 and at least one closure body system 150,152 can be provided for the tibia component 104. The mechanical reel 140 is attached to the appropriate component 102, 104 or alternatively to the closure body system 150, 152 wing 162, 164 or closure body 156. The lace 142 is threaded through the channels 158 and the guides 165 of the wings 162, 164 so that they are able to be drawn in and tightened by turning the mechanical reel 140.

The mechanical wheel 140 allows for precise tightening of the lace 142 in order to fine tune, and then lock in, the amount of compression provided to the leg by the brace 100. The lace 142 can be steel, nylon or other non-stretchable material. A lace 142 constructed of steel or other suitable metal provides superior resistance to chewing by the animal during the duration of wearing brace 100.

The mechanical wheel 140 can be designed so that its low profile or material resists chewing. In another embodiment, the mechanical wheel 140 can be covered with a cover 141 as is depicted in FIG. 4. The cover 141, as shown, may comprise a conical shape, and is configured to completely cover the mechanical reel 140. Openings (not shown) are provided at the outer edges of cover 141 allowing the laces 142 to pass through unimpeded. The cover 141 can be manufactured from plastic or metal so long as the profile of cover 141 is such that an animal biting at the cover could not grip the cover between its teeth. In other embodiments, the cover 141 can be a pyramid, or a partial spherical or ovoid shape. In embodiments where reel 140 is located on closure body 156, the profile of component 102, 104 may be relieved or scalloped for clearance as necessary to allow sufficient tightening of brace 100.

In another embodiment, as depicted in FIG. 2b, a hock component 103 is provided. The hock component 103, as illustrated, is provided with a body closure system but the hock component 103 can also be provided and used without a body closure system.

The hock component 103 can be used as part of the brace system 101, used alone, or used in combination with only the tibia component 104. Attached to the hock component 103 is a secondary upper stabilization bar 107, a secondary lower stabilization bar 109, a secondary hinge 111, secondary lower adjustment screws 117, secondary upper adjustment screws 115, and a closure system 116. The brace 101 can also feature an optional paw cover 200 attached to the hock component 103. The hock component 103 can be provided in alternate standard sizes.

According to various embodiments, the braces described herein are configured to be modular, such that various combinations of component 102, component 104, component 103 and paw cover 200 may be utilized as desired for to treat different injuries. For example, to treat a metatarsal or metacarpal injury, a single component 103 may be provided. To provide additional immobilization to the limb, for example to treat an Achilles injury or an elbow injury, component 104 and stabilization bars may be added to component 103. To provide further immobilization, for example to treat a cranial cruciate ligament injury, component 102 and stabilization bars may be added to component 104 and component 103.

The hock component 103 is made of a composite material of the type described in U.S. Published Patent Application No. 2012/01011417 to Joseph, the disclosure of which is incorporated by reference herein in its entirety. As described therein, the composite material generally includes an inner foam layer for comfort, a middle thermoformable polymer material, and an outer layer of durable fabric. In one embodiment, the outer layer can be made of an unbroken loop material. In another embodiment, the hock component 103 is constructed of a material such as described in U.S. patent application Ser. No. 13/836,660 to Joseph, filed Mar. 15, 2013 and titled "Foam Core Sandwich Splint," the disclosure of which has been incorporated by reference.

The hock component 103 is provided to a veterinarian pre-formed into a general u-shape and is of a specified length. The veterinarian heats the hock component 103, generally using a dry heat source, making the material malleable and able to be further custom formed to the animals limb, in the veterinarian's office. Heating can be accomplished using, for example, ovens, convection ovens, radiant lamp heat sources, infrared heaters, microwave ovens, self heating pouches, internal heating system built into the material, or exothermic heating source. In addition, wet heat can be used, for example, immersion of the material into hot water.

While the material is hot and malleable, the veterinarian places the material on the limb below the hock joint and above the paw and forms the material around the limb to obtain a precise custom fit. As the material cools, the material becomes rigid and retains the shape of the limb. An advantage of using the composite material is that the hock component 103 can be molded and custom fitted in the veterinarian's office without the need to make a casting or send the hock component 103 to an outside laboratory. Another advantage is that due to the dry heating methods the hock component 103 can be applied immediately after surgery versus a cast or other splint that may require wetting in order to form it thus introducing moisture to the incision area.

The veterinarian chooses the material based on the size of the animal so that the material, when formed, fits substantially around the circumference of the limb leaving a longitudinal opening 148 at the front or anterior of the limb. Thus, when formed, the hock component 103 forms a substantially u-shaped channel 145, where the ends 146 of the u-shaped channel 145 do not touch. The opening 148 allows for easy placement and removal of the hock component 103 since the ends 146 of the u-shaped channel 145, though rigid, can be easily spread apart in order to place the limb into the u-shaped channel 145 between the ends 146 of the u-shaped channel 145. In an alternate embodiment, the hock component 103 can be formed such that the longitudinal opening 148 can be located at the posterior or rear of the limb.

In another embodiment, the hock component 103 is molded so that the ends 146 of the u-shaped channel 145 overlap when formed to the limb.

As depicted in FIG. 2b, an external frame provides connectivity between the hock component 103 and the tibia component 104. The external frame has a secondary upper stabilization bar 107 attached to the tibia component 104 and a secondary lower stabilization bar 109 attached to the hock component 103. The stabilization bars 107, 109 can be designed to be linearly adjustable in relation to the tibia component 104 and the hock component 103. Alternatively, the stabilization bars 107, 109 can be designed to be non-adjustable in relation to the tibia component 104 and the hock component 103. Attachment of the stabilization bars 107, 109 to the components 103, 104 can be made as depicted in the embodiment of FIG. 2b with the use of adjustment screws 115, 117 and threaded receivers that are molded into or otherwise engaged with the lightweight composite material. Other embodiments contemplate other methods of attaching the stabilization bars 107, 109 to the components 103, 104 including other known fasteners such as nuts, bolts, rivets, pins, retaining rings, clips, etc. Other embodiments contemplate that attachment of the stabilization bar 107, 109 to the lightweight composite material of the hock component 103 or tibia component 104 can be made by the use of crimping, gluing, soldering, cementing, adhesives, etc. or incorporation of the stabilization bar 107, 109 into the lightweight composite material of the hock component 103 or tibia component 104.

One embodiment provides that the upper stabilization bar 107 and lower stabilization bar 109 are linearly adjustable in relation to the components 103, 104 via bar adjustment slots 121 at their distal ends 123, 125. The slots 121 are sized to be smaller than the head of the adjustment screws 115, 117 so that tightening of the screws 115, 117 cause the heads to compress the stabilization bars 107, 109 against the components 103, 104 preventing the stabilization bars 107, 109 from moving in relation to the components 103, 104. In the embodiment illustrated, the adjustment screws 115, 117 are thumbscrews but they can be any type of fastener that can be tightened including, wingnuts, nuts, ratchets, screws, etc.

Other embodiments, as illustrated in FIG. 3, can incorporate separate openings 118 in the stabilization bars 107, 109 that are longitudinally evenly spaced. The openings 118 can be sized to accept pins, screws, push-button adjustments, etc. The openings 118 can be any shape including round, square, triangular, etc.

The proximal end 127 of the secondary upper stabilization bar 107 engages with the proximal end 129 of the secondary lower stabilization bar 109 and forms an orthopedic hinge assembly 111. In one embodiment, the hinge assembly 111 can be a full range of motion (ROM) hinge maintaining selective ranges of flexion and extension. Other embodiments can incorporate other hinges known in the art, for example, single pivot hinges, dual pivot hinges, and veterinary TAMARACK FLEXURE JOINTS®. The hinge assembly 111 can be designed so that it can be used in a locked position preventing any rotation or unlocked allowing limited to full rotation.

The upper stabilization bar 107 and lower stabilization bar 109 can be configured so that the profile of the stabilization bars 107, 109 follow the contours of the animal's leg. An alternate embodiment allows for the upper stabilization bar 107 and lower stabilization bar 109 to be substantially flat. It is contemplated that alternate configurations of upper stabilization bar 107 and lower stabilization bar 109 can be incorporated, e.g., a contoured upper stabilization bar 107 paired with a flat lower stabilization bar 109 or vice versa.

The closure system 116 has a mechanical reel 140 and lace 142 to provide smooth, even closure of the hock component 103 with no pressure points. Reel 140 is preferably of the type available from Boa Technology, such as described in U.S. Pat. Nos. 5,934,599, 6,202,953, 6,289,558, 7,950,112, 7,954,204, 7,992,261, and 8,091,182, the disclosures of which are incorporated by reference herein. Alternatively, other fastening mechanisms such as cord locks, cam cord locks, traditional lacing bows, ratchet lace systems, or other lacing methods may be used in place of any of the closure systems described herein.

At least one closure system 116 can be provided for the hock component 103. The mechanical reel 140 is attached to the hock component 103 at a convenient location. There are no restrictions as to where the mechanical reel can be attached as long as the lace 142 and the reel 140 are not impeded by other structures on the hock component 103. In one embodiment, the reel 140 is located on the posterior side of the hock component 103. In another embodiment, the reel 140 is located on the side of the hock component 103. In another embodiment, reel 140 is location on the anterior side.

The mechanical reel allows for the lace 142 to be drawn in and tightened by turning the mechanical reel 140. The mechanical wheel 140 allows for precise tightening of the lace 142 in order to fine tune, and then lock in, the amount of compression provided to the leg by the hock component 103. The lace 142 can be, for example, steel, nylon or other non-stretchable material. A lace 142 constructed of steel or other suitable metal provides superior resistance to chewing by the animal during the duration of wearing the hock component 103. The lace 142 is threaded through guides 166 that are molded into or otherwise engaged with the lightweight composite material. In one embodiment, the guides 166 are a plurality of nylon sleeves or loops. In another embodiment, the guides 166 can be made of the lightweight composite material, plastic, metal or another suitable material and form a protrusion having an aperture that the lace 142 is threaded through. In some embodiments, the guides 166 are placed longitudinally along the hock component 103 so that they are substantially parallel to each other on either side of the u-shaped channel 145.

The mechanical wheel 140 can be designed so that its low profile or material resists chewing. In another embodiment, the mechanical wheel 140 can be covered with a cover 141 as is depicted in FIG. 4. The cover 141, as shown, may comprise a conical shape, and is configured to completely cover the mechanical reel 140. Openings (not shown) are provided at the outer edges of cover 141 allowing the laces 142 to pass through unimpeded. The cover 141 can be manufactured from plastic or metal so long as the profile of cover 141 is such that an animal biting at the cover could not grip the cover between its teeth. In other embodiments, the cover 141 can be a pyramid, or a partial spherical or ovoid shape.

In another embodiment, the hock component 103 is provided with a closure body system 151 as is described above in relation to the femur component 102 and the tibia component 103. For brevity sake, the closure body system 151 is formed and fitted identically to the closure body systems 150, 152 described above but in relation to the hock component 103, thus the same reference numbers will be used.

The closure body 156 of the closure body system 151 can be made of the same lightweight composite material as the component 103 and is heated and subsequently formed to the appropriate portion of the animals limb. Alternatively, the closure body 156 can be provided so that it has a preformed u-shaped channel along its length. Alternatively, the closure body 156 can be made of another flexible material that can be shaped. The closure body 156 is sized so that when placed on the limb of the animal, it fits partially around the circumference of the animals limb. In one embodiment, a plurality of guides 158 may be located on the closure body 156 and are substantially perpendicular to the longitudinal axis 160 of the closure body 156.

FIGS. 8 and 9 illustrate the component 103 having a closure system 151 in the closed and open positions, respectively. As illustrated in FIG. 8, when closed, the closure body 156 preferably sits on the animals limb so that when the component 103 is positioned, the ends 146 of the u-shaped channel 145 overlap the closure body 156 sandwiching the closure body 156 between the ends 146 of the u-shaped channel 145 and the animals limb. Thus, the outer surface 168 of the closure body 156 slidably engages with the inner surface 166 of the component 103.

The closure system 151 has a first wing 162 made from the hook portion of a hook and loop woven material and a second wing 164 made from either woven material or the hook portion of a hook and loop woven material. Alternatively, more than two wings can be provided. The wings 162, 164 are provided with a plurality of guides 165 that are placed linearly along the length of the wings 162, 164 either on the edge of the wing 162, 164 or on the topside of the wing 162, 164. In one embodiment, the guides 165 are a plurality of nylon sleeves. In another embodiment, the guides 165 are a plurality of loops made from a woven material.

The hook material of the bottom side of the first wing 162 complements the unbroken loop fabric covering the brace. In another embodiment, the hook material of the bottom side of the first wing 162 complements the loop portion of the hook and loop closure 154 provided on the at least one outer side of the component 103 thereby providing adhesion with the material on the at least one outer side of the component 103. Thus, the wing 162 is adhered with the component 103 surface opposite that of the animals limb. One advantage in providing a hook and loop closure is that the closure system 151 can be detached from at least one side of the component 103 allowing for easy insertion or removal of the animals limb into or out of the component 103.

The second wing 164 can be made of a woven material. As depicted in FIG. 9, the woven material of the second wing 164 can be fixedly attached to the outer side of the component 103 so that the wing 164 is on the component 103 surface opposite that of the animals limb. Attachment can be by any manner that permanently attaches the woven material to the component 103, for example, by adhesives, sewing, rivets, etc. Alternatively, the second wing 164 can be comprised of the hook of the hook and loop woven material and can be detachably connected to the unbroken loop fabric covering the component 103 surface. In another embodiment, the hook provides adhesion to the loop portion of a hook and loop closure 154 provided on the at least one outer side of the component 103 so that the wing 164 adheres with the component 103 surface opposite that of the animals limb.

The closure body system 151 further comprises a closure system 116 having a mechanical reel 140 and lace 142 to provide smooth, even closure of the brace 100 with no pressure points. Reel 140 is preferably of the type available from Boa Technology, such as described in U.S. Pat. Nos. 5,934,599, 6,202,953, 6,289,558, 7,950,112, 7,954,204, 7,992,261, and 8,091,182, the disclosures of which are incorporated by reference herein. Alternatively, other fastening mechanisms such as cord locks, cam cord locks, traditional lacing bows, ratchet lace systems, or other lacing methods may be used in place of any of the closure systems described herein.

At least one closure body system 151 can be provided for the hock component 103. The mechanical reel 140 is attached to the hock component 103 or alternatively to the closure body system 151 wing 162, 164 or closure body 156. The lace 142 is threaded through the optional channels 158 and the guides 165 of the wings 162, 164 so that they are able to be drawn in and tightened by turning the mechanical reel 140. The mechanical wheel 140 allows for precise tightening of the lace 142 in order to fine tune, and then lock in, the amount of compression provided to the leg by the brace 100. The lace 142 can be steel, nylon or other non-stretchable material. A lace 142 constructed of steel or other suitable metal provides superior resistance to chewing by the animal during the duration of wearing brace 100.

The mechanical wheel 140 can be designed so that its low profile or material resists chewing. In another embodiment, the mechanical wheel 140 can be covered with a cover 141 as is depicted in FIG. 4. The cover 141, as shown, may comprise a conical shape, and is configured to completely cover the mechanical reel 140. Openings (not shown) are provided at the outer edges of cover 141 allowing the laces 142 to pass through unimpeded. The cover 141 can be manufactured from plastic or metal so long as the profile of cover 141 is such that an animal biting at the cover could not grip the cover between its teeth. In other embodiments, the cover 141 can be a pyramid, or a partial spherical or ovoid shape.

In one embodiment, a paw cover 200 can be provided and attached to the hock component 103. The paw cover 200 is provided in a variety of sizes and can be selected to conform generally to the size of the paw. As depicted in FIGS. 16 and 17, the paw cover 200 can be pre-formed into a general u-shape providing a natural stance for the paw of a canine. The paw cover 200 can be made of a lightweight composite material including at least one layer of thermoformable material. The paw cover 200 is sized such that the distal end 202 ends below the hind foot hock or the forefoot wrist of the canine. The proximal end 204 of the paw cover 200 is located near or at the end of the canine's foot. The paw cover 200 can be provided with an adjustment slot 206 extending longitudinally from the distal end 202. The adjustment slot 206 is provided to attach the paw cover 200 to the hock component 103 as depicted in FIG. 2b. The hock component 103 can be provided with at least two adjustment screws located on its posterior (not shown). The paw cover 200 is disposed so that the shaft or threaded portion of the adjustment screws reside in the adjustment slot 206 so that when tightened, paw cover is sandwiched between the head of the adjustment screw and the hock component 103 thus fixedly attaching the paw cover 200 to the hock component 103.

In another embodiment, separate adjustment openings (not shown) can be provided in the paw cover 200. The separate openings can be evenly spaced longitudinally along the paw cover 200 posterior. The openings can be sized to accept pins, screws, push-button adjustments, etc. The openings can be any shape including round, square, triangular, etc.

In another embodiment, as depicted in FIG. 13, a formed splint 170 is provided that includes a semi-customizable first splint component 171 and a closure system 116 attachable in any position and adjustable as desired, allowing customizable, universal fitment for a variety of uses. The formed splint 170 is provided in alternate standard sizes. It is understood that the splint 170 can be configured to be incorporated into the brace 100 system as described above.

The semi-customizable first splint component 171 is made of a composite material of the type described in U.S. Published Patent Application No. 2012/01011417 to Joseph, the disclosure of which is incorporated by reference herein in its entirety. As described therein, the composite material generally includes an inner foam layer for comfort, a middle thermoformable polymer material, and an outer layer of durable fabric. In another embodiment, the semi-customizable first splint component 171 is constructed of a material such as described in U.S. patent application Ser. No. 13/836, 660 to Joseph, filed Mar. 15, 2013 and titled "Foam Core Sandwich Splint," the disclosure of which has been incorporated by reference.

The first splint component 171 is provided to a veterinarian pre-formed into a general u-shape and is of a specified length. The veterinarian heats the first splint component 171, generally using a dry heat source, making the material malleable and able to be further custom formed to the animals limb, in the veterinarian's office. Heating can be accomplished using, for example, ovens, convection ovens, radiant lamp heat sources, infrared heaters, microwave ovens, self heating pouches, internal heating system built into the material, or exothermic heating source. In addition, wet heat can be used, for example, immersion of the material into hot water.

While the material is hot and malleable, the veterinarian places the material on the appropriate area of the animals limb and forms the material around the limb to obtain a precise custom fit. As the material cools, the material becomes rigid and retains the shape of the limb. An advantage of using the composite material is that the first splint component 171 can be molded and custom fitted in the veterinarian's office without the need to make a casting or send the first splint component 171 to an outside laboratory. Another advantage is that due to the dry heating methods the splint can be applied immediately after surgery versus a cast or other splint that may require wetting in order to form it thus introducing moisture to the incision area.

The veterinarian chooses the material based on the size of the animal so that the material, when formed, fits substantially around the circumference of the limb leaving a longitudinal opening 176 at the front or anterior of the limb. Thus, when formed, the first splint component 171 forms a substantially u-shaped channel 172, where the ends 174 of the u-shaped channel 172 do not touch. The opening 176 allows for easy placement and removal of the first splint component 171 since the ends 174 of the u-shaped channel 172, though rigid, can be easily spread apart in order to place the limb into the u-shaped channel 172 between the ends 174 of the u-shaped channel 172. In an alternate embodiment, the first splint component 171 can be formed such that the longitudinal opening 176 can be located at the posterior or rear of the limb.

In another embodiment, the first splint component 171 is molded so that the ends 174 of the u-shaped channel 172 overlap when formed to the limb.

Figure 14:
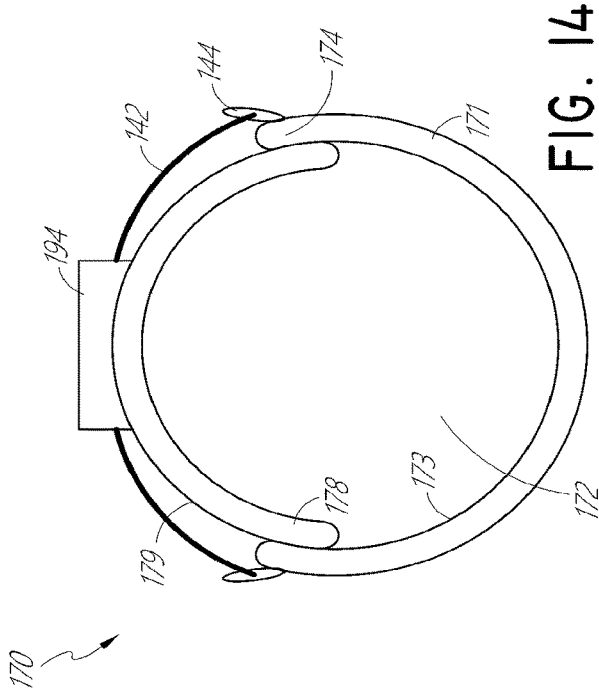
FIG. 14 is a cross sectional view of the animal orthopedic splint type brace incorporating a first splint component and a second splint component.

A second splint component 178, as depicted in FIG. 14, is provided that partially encompasses the circumference of the limb and is comparable in length to the length of the first splint component 171. As depicted, the second splint component 178 is worn so that when the first splint component 171 is placed in position, the ends 174 of the u-shaped channel 172 overlap the ends of the second splint component 178 longitudinally. The second splint component 178 is thus partially sandwiched between the limb and the first splint component 171. Thus, the outer surface 179 of the second splint component 178 slidably engages with the inner surface 173 of the first splint component 171.

The second splint component 178 is made of a composite material of the type described in U.S. Published Patent Application No. 2012/01011417 to Joseph, the disclosure of which is incorporated by reference herein in its entirety. As described therein, the composite material generally includes an inner foam layer for comfort, a middle thermoformable polymer material, and an outer layer of durable fabric. In another embodiment, the customizable second splint component 178 is constructed of a material such as described in U.S. patent application Ser. No. 13/836,660 to Joseph, filed Mar. 15, 2013 and titled "Foam Core Sandwich Splint," the disclosure of which has been incorporated by reference.

The formed splint 170 includes an attached closure system 116 having a mechanical reel 140 and lace 142 to provide smooth, even closure of the brace 100 with no pressure points. Reel 140 is preferably of the type available from Boa Technology, such as described in U.S. Pat. Nos. 5,934,599, 6,202,953, 6,289,558, 7,950,112, 7,954,204, 7,992,261, and 8,091,182, the disclosures of which are incorporated by reference herein. Alternatively, other fastening mechanisms such as cord locks, cam cord locks, traditional lacing bows, ratchet lace systems, or other lacing methods may be used in place of any of the closure systems described herein.

The closure system 116 uses a mechanical reel 140 and lace 142 to provide smooth, even closure of the splint component 171 with no pressure points. At least one closure system 116 can be provided for the splint 170. The mechanical reel 140 is attached to the posterior of the splint component 171. Alternatively, the reel 140 can be attached to the side of the splint component 171. The mechanical reel allows for the lace 142 to be drawn in and tightened by turning the mechanical reel 140. The mechanical wheel 140 allows for precise tightening of the lace 142 in order to fine tune, and then lock in, the amount of compression provided to the limb by the splint component 171. The lace 142 can be steel, nylon or other non-stretchable material. A lace 142 constructed of steel or other suitable metal provides superior resistance to chewing by the animal during the duration of wearing brace 100. The lace 142 is threaded through guides 144 that are molded into or otherwise engaged with the composite material. In one embodiment, the guides 144 are a plurality of nylon sleeves or loops. In another embodiment, the guides 144 can be made of the composite material, plastic, metal or another suitable material and form a protrusion having an aperture that the lace 142 is threaded through. The guides 144 are placed longitudinally along the splint component 171 so that they are substantially parallel to each other on either side of the u-shaped channel 172. The closure system 116 allows for adjustability, to a micro level, to accommodate swelling and/or atrophy.

The mechanical wheel 140 can be designed so that its low profile or material resists chewing. In another embodiment, the mechanical wheel 140 can be covered with a cover 141 as is depicted in FIG. 4. The cover 141, as shown, may comprise a conical shape, and is configured to completely cover the mechanical reel 140. Openings (not shown) are provided at the outer edges of cover 141 allowing the laces 142 to pass through unimpeded. The cover 141 can be manufactured from plastic or metal so long as the profile of cover 141 is such that an animal biting at the cover could not grip the cover between its teeth. In other embodiments, the cover 141 can be a pyramid, or a partial spherical or ovoid shape.

Figure 15:
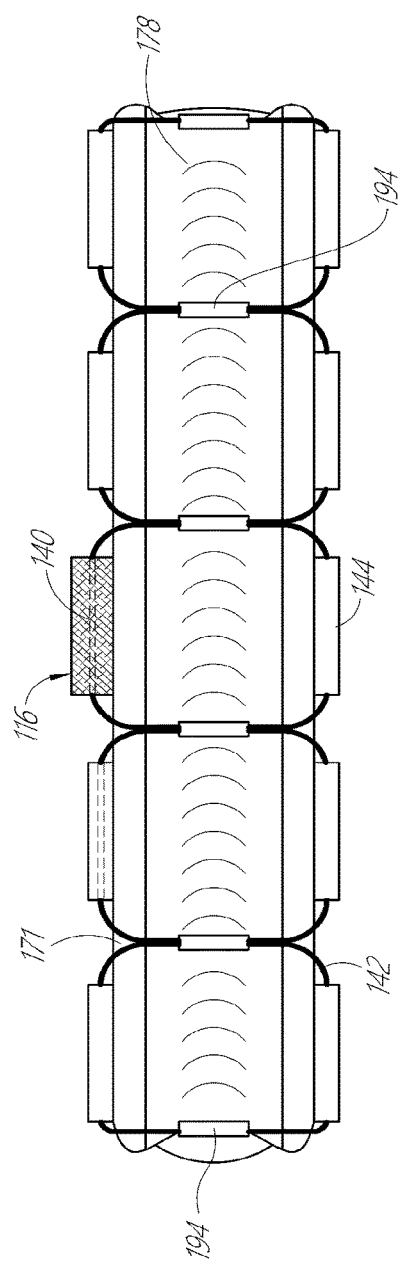
FIG. 15 is a front view of the semi-customizable animal orthopedic splint type brace having a first splint component and a second splint component, the second splint component provided with lacing guides.

In one embodiment, lacing guides 194 can be provided on the second splint component 178, as is depicted in FIGS. 14 and 15. The guides 194 are attached to the second splint component 178 thus providing a pathway for the lace 142. In an alternate embodiment, the second splint component 178 is not provided with guides 194.

Figure 10:
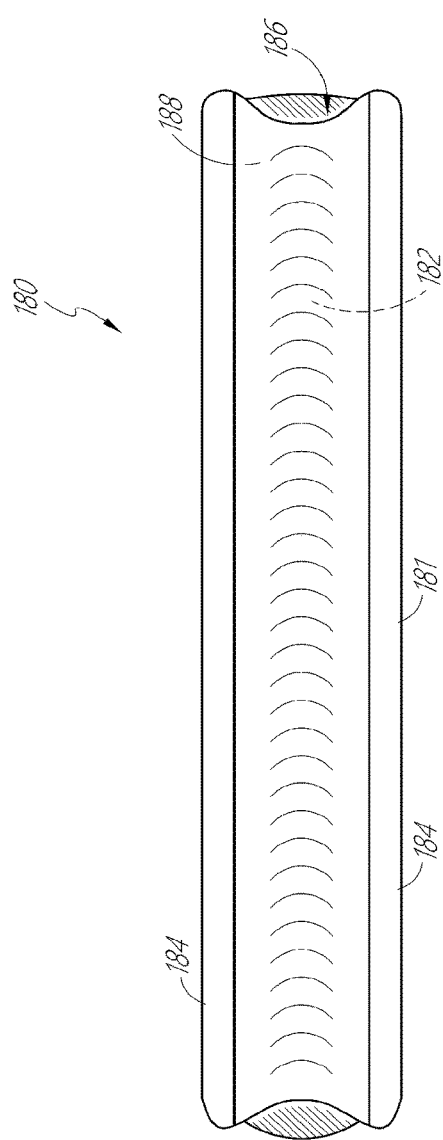
FIG. 10 is a front view of the animal orthopedic dual-valve splint having a first splint component and a second splint component.
Figure 11:
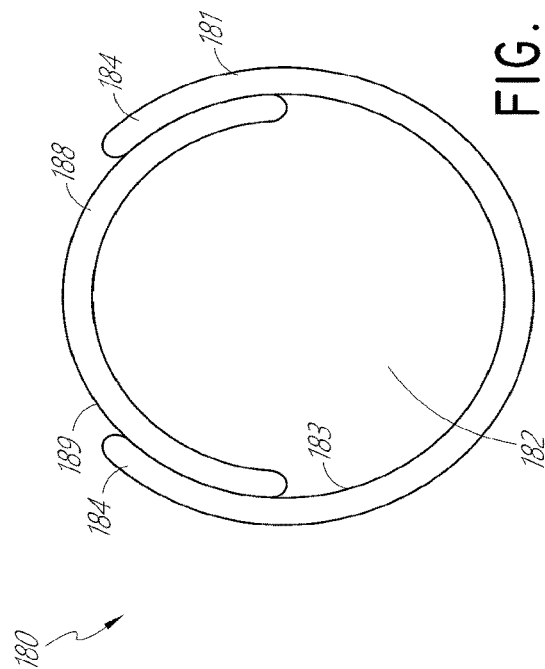
FIG. 11 is a cross sectional view of the animal orthopedic dual-valve splint incorporating a first splint component and a second splint component.

In another embodiment, a dual-valve splint-type brace is provided. The dual-valve splint 180 as illustrated in FIGS. 10 and 11 depicts an embodiment of an animal orthopedic splint configured to support and stabilize the limb of an animal. Where the features of this embodiment are comparable to the features of FIGS. 1 and 2, the same reference numbers will be used. In addition, for the sake of brevity, description is only provided for those features of this embodiment that are not provided in the embodiment as depicted in FIGS. 1 and 2.

The dual-valve splint 180 can be applied as a prophylactic device to prevent or reduce the severity of an injury, as a rehabilitative device to support and stabilize a limb while restricting motion, or as a functional device to provide stability for long term support and function. The dual-valve splint 180 is generally comprised of a first splint component (or valve) 181, a second splint component (or valve) 188, and a removable tensioning system (as depicted in FIG. 12). The dual-valve splint 180 may be provided in the form of a kit, including one or more sheets of composite material, at least one universal removable tensioning system, and optionally a set of instructions for use to create a splint from the materials of the kit. The instructions may be provided as part of the kit, or indications may be provided linking a user to electronically accessible instructions. Alternately, dual-valve splint 180 may be provided in the form of various pre-sized sheets of composite material, at least one universal removable tensioning system, and optionally instructions for use to create a splint from the materials of the kit.

The customizable first splint component 181 is made of a composite material of the type described in U.S. Published Patent Application No. 2012/01011417 to Joseph, the disclosure of which is incorporated by reference herein in its entirety. As described therein, the composite material generally includes an inner foam layer for comfort, a middle thermoformable polymer material, and an outer layer of durable fabric. The inner foam layer can be replaceable. In another embodiment, the customizable first splint component 181 is constructed of a material such as described in U.S. patent application Ser. No. 13/836,660 to Joseph, filed Mar. 15, 2013 and titled "Foam Core Sandwich Splint," the disclosure of which has been incorporated by reference.

The first splint component 181 can be provided to a veterinarian as a flat sheet, or pre-formed into a general u-shape. The veterinarian heats the first splint component 181, generally using a dry heat source, making the material malleable and able to be further custom formed to the animals limb, in the veterinarian's office. Heating can be accomplished using, for example, ovens, convection ovens, radiant lamp heat sources, infrared heaters, microwave ovens, self heating pouches, internal heating system built into the material, or exothermic heating source. In addition, wet heat can be used, for example, immersion of the material into hot water.

While the material is hot and malleable, the veterinarian places the material on the appropriate area of the animals limb and forms the material around the limb to obtain a precise custom fit. In addition, prior to heating or after heating, the material can be trimmed as necessary to custom form the material as necessary, e.g., leave incision sites uncovered or form to provide an angular configuration. As the material cools, the material becomes rigid and retains the shape of the limb. An advantage of using the composite material is that the first splint component 181 can be molded and custom fitted in the veterinarian's office without the need to make a casting or send the first splint component 181 to an outside laboratory. Another advantage is that due to the dry heating methods the splint can be applied immediately after surgery versus a cast or other splint that may require wetting in order to form it thus introducing moisture to the incision area.

The veterinarian chooses the material based on the size of the animal so that the material, when formed, fits substantially around the circumference of the limb leaving a longitudinal opening 186 at the front or anterior of the limb. Thus, when formed, the first splint component 181 forms a substantially u-shaped channel 182, as depicted in FIG. 10, where the ends 184 of the u-shaped channel 182 do not touch. The opening 186 allows for easy placement and removal of the first splint component 181 since the ends 184 of the u-shaped channel 182, though rigid, can be easily spread apart in order to place the limb into the u-shaped channel 182 between the ends 184 of the u-shaped channel 182. In an alternate embodiment, the first splint component 181 can be formed such that the longitudinal opening 186 can be located at the posterior or rear of the limb.

In another embodiment, the first splint component 181 is molded so that the ends 184 of the u-shaped channel 182 overlap when formed to the limb.

A second splint component 188, as depicted in FIG. 11, can be provided that partially encompasses the circumference of the limb and is cut to be comparable in length to the length of the first splint component 181. As depicted, the second splint component 188 is worn so that when the first splint component 181 is placed in position, the ends 184 of the u-shaped channel 182 overlap the ends of the second splint component 188 longitudinally. The second splint component 188 is thus partially sandwiched between the limb and the first splint component 181. Thus, the outer surface 189 of the second splint component 188 slidably engages with the inner surface 183 of the first splint component 181.

The second splint component 188 is made of a composite material of the type described in U.S. Published Patent Application No. 2012/01011417 to Joseph, the disclosure of which is incorporated by reference herein in its entirety. As described therein, the composite material generally includes an inner foam layer for comfort, a middle thermoformable polymer material, and an outer layer of durable fabric. The outer fabric is comprised of an unbroken loop fabric. The inner foam layer can be replaceable. In another embodiment, the customizable second splint component 188 is constructed of a material such as described in U.S. patent application Ser. No. 13/836,660 to Joseph, filed Mar. 15, 2013 and titled "Foam Core Sandwich Splint," the disclosure of which has been incorporated by reference.

The dual-valve splint 180 can be provided with a detachable tensioning system 190, as illustrated in FIG. 12. The dual-valve splint 180 is not provided with a closure system 116 integral to the dual-valve splint 180 but instead is provided with a tensioning system 190 that is removably attached after forming the dual-valve splint 180 to the limb. The tensioning system 190 uses a mechanical reel 140 and lace 142 to provide smooth, even closure of the splint 180 with no pressure points. Reel 140 is preferably of the type available from Boa Technology, such as described in U.S. Pat. Nos. 5,934,599, 6,202,953, 6,289,558, 7,950,112, 7,954,204, 7,992,261, and 8,091,182, the disclosures of which are incorporated by reference herein. Alternatively, other fastening mechanisms such as cord locks, cam cord locks, traditional lacing bows, ratchet lace systems, or other lacing methods may be used in place of any of the closure systems described herein.

The tensioning system 190 has a plurality of wings 192, the plurality being one up to whatever number the veterinarian deems appropriate. The wings 192 are made from either the hook portion of a hook and loop woven material and can be rectangular in shape. In other embodiments, the shape of the wings 192 can be circular, square, triangular or a combination thereof. One edge portion of the wing 192 is provided with a guide 196 that is placed linearly along the edge of the wing 192. The guide 196 is encompassed as part of the wing 192 material.

As noted, the wing 192 is comprised of the hook portion of the hook and loop woven material. This hook complements the material of the outer surface of the first splint component 181 so the wing is removably attached to the outer surface of the first splint component 181. One advantage in providing a hook and loop closure is that the tensioning system 190 can be detached from the first splint component 181 allowing for easy insertion or removal of the animals limb into or out of the splint 180. Another advantage is that based on the animal's anatomy, the tensioning system 190 can be placed wherever needed.

At least one tensioning system 190 can be provided for the dual-valve splint 180. The mechanical reel 140 can be attached to a wing 192 or alternatively, the reel 140 can be removably attached via a hook and loop material to the body of the dual-valve splint 180. The lace 142 is threaded through the wing guides 196 allowing the dual-valve splint 180 to be drawn in and tightened by turning the mechanical reel 140. The mechanical wheel 140 allows for precise tightening of the lace 142 in order to fine tune, and then lock in, the amount of compression provided to the limb by the dual-valve splint 180. The lace 142 can be steel, nylon or other non-stretchable material. A lace 142 constructed of steel or other suitable metal provides superior resistance to chewing by the animal during the duration of wearing brace 100.

The tensioning system 190 allows for adjustability, to a micro level, to accommodate swelling and/or atrophy.

The mechanical wheel 140 can be designed so that its low profile or material resists chewing. In another embodiment, the mechanical wheel 140 can be covered with a cover 141 as is depicted in FIG. 4. The cover 141, as shown, may comprise a conical shape, and is configured to completely cover the mechanical reel 140. Openings (not shown) are provided at the outer edges of cover 141 allowing the laces 142 to pass through unimpeded. The cover 141 can be manufactured from plastic or metal so long as the profile of cover 141 is such that an animal biting at the cover could not grip the cover between its teeth. In other embodiments, the cover 141 can be a pyramid, or a partial spherical or ovoid shape.

Figure 18:
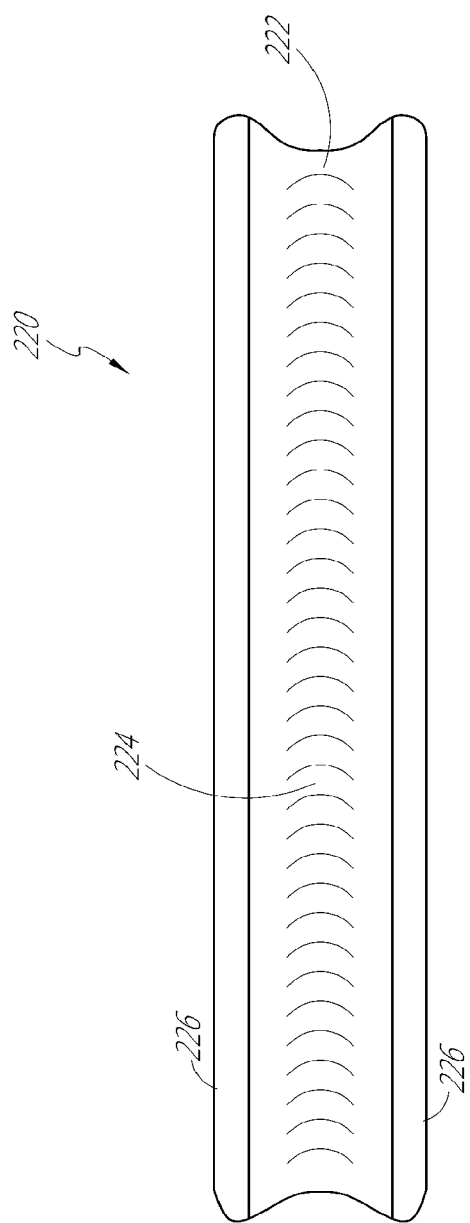
FIG. 18 is a top view of a basic splint.

In another embodiment, a basic splint is provided. The basic splint 220 as illustrated in FIG. 18 depicts an embodiment of an animal orthopedic splint configured to support and stabilize the limb of an animal. The basic splint 220 can be applied as a prophylactic device to prevent or reduce the severity of an injury, as a rehabilitative device to support and stabilize a limb while restricting motion, or as a functional device to provide stability for long term support and function. The basic splint 220 is made of a composite material of the type described in U.S. Published Patent Application No. 2012/01011417 to Joseph, the disclosure of which is incorporated by reference herein in its entirety. As described therein, the composite material generally includes an inner foam layer for comfort, a middle thermoformable polymer material, and an outer layer of durable fabric. The inner foam layer can be replaceable. In another embodiment, the basic splint 220 is constructed of a material such as described in U.S. patent application Ser. No. 13/836,660 to Joseph, filed Mar. 15, 2013 and titled "Foam Core Sandwich Splint," the disclosure of which has been incorporated by reference.

The basic splint 220 can be provided to a veterinarian pre-formed into a general u-shape. The veterinarian heats the basic splint 220, generally using a dry heat source, making the material malleable and able to be further custom formed to the animals limb, in the veterinarian's office. Heating can be accomplished using, for example, ovens, convection ovens, radiant lamp heat sources, infrared heaters, microwave ovens, self heating pouches, internal heating system built into the material, or exothermic heating source. In addition, wet heat can be used, for example, immersion of the material into hot water.

While the material is hot and malleable, the veterinarian places the material on the appropriate area of the animals limb and forms the material around the limb to obtain a precise custom fit. In addition, prior to heating or after heating, the material can be trimmed as necessary to custom form the material as necessary, e.g., shorten the length, leave incision sites uncovered or form to provide an angular configuration. As the material cools, the material becomes rigid and retains the shape of the limb. An advantage of using the composite material is that the basic splint 220 can be molded and custom fitted in the veterinarian's office without the need to make a casting or send the basic splint 220 to an outside laboratory. Another advantage is that due to the dry heating methods the splint can be applied immediately after surgery versus a cast or other splint that may require wetting in order to form it thus introducing moisture to the incision area.

The veterinarian chooses the material based on the size of the animal so that the material, when formed, fits substantially around the circumference of the limb leaving a longitudinal opening 222 at the front or anterior of the limb. Thus, when formed, the basic splint 220 forms a substantially u-shaped channel 224, as depicted in FIG. 18, where the ends 226 of the u-shaped channel 224 do not touch. The opening 222 allows for easy placement and removal of the basic splint 220 since the ends 226 of the u-shaped channel 224, though rigid, can be easily spread apart in order to place the limb into the u-shaped channel 224 between the ends 226 of the u-shaped channel 224. In an alternate embodiment, the longitudinal opening 222 can be located at the posterior or rear of the limb.

In another embodiment, the basic splint 220 is molded so that the ends 226 of the u-shaped channel 224 overlap when formed to the limb.

The base splint 220 can be circumferentially wrapped and tensioned as desired using various known tensioning techniques, e.g., ACE Bandages, VELCRO straps, tape, etc.

Various modifications to the embodiments of the inventions may be apparent to one of skill in the art upon reading this disclosure. For example, persons of ordinary skill in the relevant art will recognize that the various features described for the different embodiments of the inventions can be suitably combined, un-combined, and re-combined with other features, alone, or in different combinations, within the spirit of the invention. Likewise, the various features described above should all be regarded as example embodiments, rather than limitations to the scope or spirit of the inventions. Therefore, the above is not contemplated to limit the scope of the present inventions.

Persons of ordinary skill in the relevant arts will recognize that the inventions may comprise fewer features than illustrated in any individual embodiment described above. The embodiments described herein are not meant to be an exhaustive presentation of the ways in which the various features of the inventions may be combined. Accordingly, the embodiments are not mutually exclusive combinations of features; rather, the inventions may comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the embodiments of the present inventions, it is expressly intended that the provisions of Section 112, sixth paragraph of 35 U.S.C. are not to be invoked unless the specific terms "means for" or "step for" are recited in a claim.

The invention claimed is:

1. A brace comprising:
a first component configured to wrap at least partially circumferentially around a hock of a limb of an animal, the first component comprising an inner surface partially surrounding a longitudinal u-shaped channel, an outer surface, and a first end of the longitudinal u-shaped channel and a second end of the longitudinal u-shaped channel, the first and second end being on opposite sides of the longitudinal u-shaped channel;
a first closure system configured to circumferentially tighten the first component around the hock of the limb of the animal;
a second component configured to wrap at least partially circumferentially around a tibia of the limb of the animal, the second component comprising a u-shaped channel having a first end and a second end;
a second closure system configured to circumferentially tighten the second component around the tibia of the limb of the animal;
first hinge assembly positioned between the first component and the second component, the first hinge assembly comprising two hinges and a first set of stabilization bars, the first set of stabilizer bars including two upper stabilizer bars each coupled to the first component and to one of the two hinges of the first hinge assembly, and the first set of stabilizer bars further including two lower stabilizer bars each coupled to the second component and to one of the two hinges, the first set of stabilizer bars configured such that an upper stabilizer bar, lower stabilizer bar, and one of the hinges are positioned on one side of the limb of the animal, and the other upper stabilizer bar, lower stabilizer bar, and hinge are positioned on the opposite side of the limb of the animal; and
a paw cover including a proximal end configured to extend below a hind foot hock or a forefoot wrist of the animal and connect to the first component, and a distal end configured to be positioned below an end of, and along the bottom of, the animal's foot, the proximal end of the paw cover including a slot and the first component including an adjustment screw, and wherein the paw cover is disposed such that a shaft of the adjustment screw is positionable along the slot to adjust the distance between the first component and the distal end of the paw cover and securable by the adjustment screw.

2. The brace of claim 1, wherein the first closure system comprises an elongated first wing having a length and width dimension, the length dimension being longer than the width dimension, the first wing comprising at least one guide, the first wing configured to releasably attach to the outer surface of the first component such that the first wing length dimension is attached along and proximal to the first end, an elongated second wing having a length and width dimension, the length dimension being longer than the width dimension, the second wing comprising at least one guide, the second wing attached to the outer surface of the first component such that the second wing length dimension is attached along and proximal to the second end, a lace inserted through the at least one guide of the first wing and the at least one guide of the second wing, and a tightening mechanism actuable to tighten the lace.

3. The brace of claim 2, wherein the second wing is configured to releasably attach to the outer surface of the first component.

4. The brace of claim 2,
wherein the second closure system comprises:
a first wing comprising at least one guide, the first wing configured to releasably attach to an outer surface of the second component proximal to the first end,
a second wing comprising at least one guide, the second wing attached to the outer surface of the second component proximal to the second end,
a lace inserted through the at least one guide of the first wing and the at least one guide of the second wing, and
a tightening mechanism actuable to tighten the lace.

5. The brace of claim 1, further comprising a cover that substantially prevents the animal from accessing the tightening mechanism.

6. The brace of claim 5, wherein the cover comprises a conical, pyramidal, partially spherical, or partially ovoidal shape.

7. The brace of claim 1, wherein the paw cover comprises a u-shape configured to provide a natural stance for the animal.

8. The brace of claim 1, wherein when the adjustment screw is tightened, the proximal end of the paw cover is sandwiched between a head of the adjustment screw and the first component.

9. The brace of claim 1, wherein the paw cover comprises a polymer layer that is thermoformable within a target temperature range and substantially rigid at temperature below 130 degrees Fahrenheit.

10. The brace of claim 1, further comprising:
a third component configured to wrap at least partially circumferentially around a femur of the limb of the animal, the third component comprising a u-shaped channel having a first end and a second end;
a third closure system configured to circumferentially tighten the third component around the femur of the limb of the animal; and
a second hinge assembly connecting the second component and the third component.

11. The brace of claim 10, wherein the third component is configured to wrap at least partially circumferentially around a femur of the animal.

12. The brace of claim 10, wherein at least one of the first component, the second component, and the third component comprises a composite material construction having:
an outer layer configured to face away from the limb of the animal; and
a polymer layer that is thermoformable within a target temperature range and substantially rigid at temperatures below 130 degrees Fahrenheit.

13. The brace of claim 10, wherein the third closure system comprises a first wing comprising at least one guide, the first wing configured to releasably attach to an outer surface of the third component proximal to the first end, a second wing comprising at least one guide, the second wing attached to the outer surface of the third component proximal to the second end, a lace inserted through the at least one guide of the first wing and the at least one guide of the second wing, and a tightening mechanism actuable to tighten the lace.

14. The brace of claim 1, wherein the first hinge assembly is configured to allow adjustment of a distance between the first component and the second component.

15. The brace of claim 14, wherein
upper stabilization bars of the first hinge assembly include an adjustment slot and
the lower stabilization bars of the first hinge assembly include an adjustment slot,
wherein the upper stabilization bars are configured to be connected to the second component by one or more fasteners extending through the adjustment slot in the upper stabilization bars, and the lower stabilization bars are configured to be connected to the first portion by one or more fasteners extending through the adjustment slot in the lower stabilization bars.

16. The brace of claim 15, wherein at least one of the upper stabilization bars or the lower stabilization bars are configured to follow contours of the limb of the animal.

17. The brace of claim 10, wherein the second hinge assembly is configured to allow adjustment of a distance between the second component portion and the third component.

18. The brace of claim 17, wherein the second hinge assembly is positioned between the second and third component, and wherein the second hinge assembly comprises:
an upper stabilization bar including an adjustment slot; and
a lower stabilization bar including an adjustment slot, the upper stabilization bar rotationally connected to the lower stabilization bar,
wherein the upper stabilization bar is configured to be connected to the third component by one or more fasteners extending through the adjustment slot in the upper stabilization bar, and the lower stabilization bar is configured to be connected to the second component by one or more fasteners extending through the adjustment slot in the lower stabilization bar.

19. The brace of claim 18, wherein at least one of the upper stabilization bar or the lower stabilization bar is configured to follow the contours of the limb of the animal.

20. The brace of claim 19, wherein the lower stabilization bar is configured to follow the contours of the limb of a dog.

* * * * *

UNITED STATES PATENT AND TRADEMARK OFFICE
CERTIFICATE OF CORRECTION

| | | |
|---|---|---|
| PATENT NO. | : 11,191,627 B2 | Page 1 of 1 |
| APPLICATION NO. | : 15/219792 | |
| DATED | : December 7, 2021 | |
| INVENTOR(S) | : Chris Boraas et al. | |

It is certified that error appears in the above-identified patent and that said Letters Patent is hereby corrected as shown below:

In the Claims

Column 27, Line 13, in Claim 15, delete "first portion" and insert -- first component --.

Column 27, Line 21, in Claim 17, delete "component portion" and insert -- component --.

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*